(12) United States Patent
Yoneda

(10) Patent No.: US 6,874,911 B2
(45) Date of Patent: Apr. 5, 2005

(54) LIGHT IRRADIATING UNIT, LIGHTING UNIT AND METHOD FOR MANUFACTURING LIGHTING UNIT

(75) Inventor: Kenji Yoneda, Kyoto (JP)

(73) Assignee: CCS, Inc., Kyoto (JP)

( * ) Notice: Subject to any disclaimer, the term of this patent is extended or adjusted under 35 U.S.C. 154(b) by 0 days.

(21) Appl. No.: 10/406,846

(22) Filed: Apr. 4, 2003

(65) Prior Publication Data

US 2003/0189831 A1 Oct. 9, 2003

(30) Foreign Application Priority Data

Apr. 9, 2002 (JP) .................................... P2002-107010
Jul. 26, 2002 (JP) .................................... P2002-218281

(51) Int. Cl.[7] .............................................. F21V 29/00
(52) U.S. Cl. ...................... 362/294; 362/373; 362/547; 362/800
(58) Field of Search ................................ 362/294, 252, 362/800, 373, 345, 264, 218, 547, 545, 240, 580, 126, 555

(56) References Cited

U.S. PATENT DOCUMENTS

| 5,632,551 A | * | 5/1997 | Roney et al. ................ 362/485 |
| 6,053,621 A | | 4/2000 | Yoneda ....................... 362/245 |
| 6,070,986 A | * | 6/2000 | Yoneda ....................... 362/33 |

* cited by examiner

Primary Examiner—Thomas M. Sember
Assistant Examiner—Bao Q. Truong

(57) ABSTRACT

A light irradiating unit is provided which is easy to manufacture with a large light production that is stable in luminous intensity and superior in life duration. The light irradiating unit comprises an illuminant loading member that has a curved illuminant loading face on which a plurality of illuminants are loaded, a holding frame that holds the illuminant loading member and a tabular heat-dissipating member that has predetermined elasticity and/or flexibility. The heat-dissipating member is attached to a back face of the illuminant loading member and a supporting face of the holding frame that faces to the back face of the illuminant loading face respectively by making use of its elasticity and/or flexibility.

12 Claims, 23 Drawing Sheets

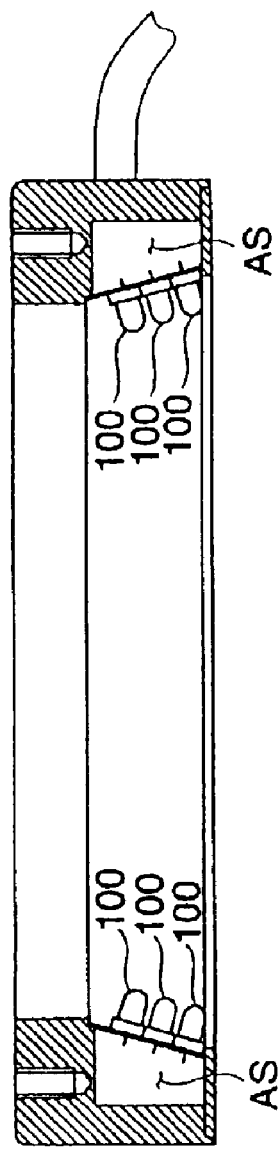

LIGHT IRRADIATING UNIT, LIGHTING UNIT AND METHOD FOR MANUFACTURING LIGHTING UNIT

BACKGROUND OF THE INVENTION AND RELATED ART STATEMENT

The present claimed invention relates to a light irradiating unit, a lighting unit and a method for manufacturing a lighting unit, more specifically to a light irradiating unit, a lighting unit and a method for manufacturing a lighting unit that is preferably used in a case of inspecting a product by making use of reflected illumination.

A light irradiating unit and a lighting unit on which a plurality of illuminants such as LEDs are arranged so as to irradiate light on an object portion to be irradiated with the illuminants surrounding the object portion so as to keep a luminous intensity of the object portion uniform has been developed.

In order to surround and cover the object portion to be irradiated, it is preferable to form an illuminant loading face in a shape of a curved concave face such as an inner face of a cylinder or a concave face of a cone frustum and a plurality of LEDs are loaded on all over the illuminant loading face. Conventionally in order to manufacture this kind of light irradiating unit, complicated manufacturing processes have been required such as a holding frame itself is formed to be an inner face of a cylinder or a concave face of a cone frustum and holes are bored on the holding frame, an illuminant is implanted into each hole and then a wiring is provided. Then the present claimed inventor has invented and patented a method for manufacturing this king of light irradiating unit in which a print substrate that can be curved are loaded with LEDs in a tabular state and then the print substrate is curved as shown in Japan Patent Laid Open No. 10-21729 in order to reduce a complicated process and a cost significantly.

However, it is extremely difficult for this kind of light irradiating unit and lighting unit to provide a heat dissipating structure in a back face of the curved illuminant loading face and actually almost no positive measure has been taken to dissipate heat. More concretely, as shown in FIG. 23, nothing is arranged in a back face of the LED 100 and there is airspace AS between the LED 100 and a holding frame. As a result of this, a temperature of the LED 100 cannot be lowered and there is much room for improvement such as a big light volume cannot be obtained, the luminous intensity is unstable and it is difficult to elongate life duration.

Further, with an arrangement in which the print substrate is curved and its flange is engaged with a holding frame the print substrate might be a little shaky or its curved face might become uneven.

In order to solve the above problems, the present claimed invention mainly intends to provide a light irradiating unit and the lighting unit in which a plurality of illuminants are arranged on a curved face that is easy to manufacture and that can get a big light volume, stable in the luminous intensity and superior in life duration.

SUMMARY OF THE INVENTION

The light irradiating unit in accordance with the present claimed invention comprises an illuminant loading member that has a curved illuminant loading face on which a plurality of illuminants are loaded, a holding frame that holds the illuminant loading member and a tabular heat-dissipating member that has predetermined elasticity and/or flexibility, and is characterized by that the heat-dissipating member is generally tightly attached to a back face of the illuminant loading face and a supporting face of the holding frame that faces to the back face of the illuminant loading face respectively by making use of the elasticity and/or flexibility.

In accordance with the invention, since the back face of the illuminant loading member and the holding frame can be joined in a surface-wise manner through the heat-dissipating member, it is possible to transmit heat generated from the illuminants effectively and quickly to the holding frame, thereby to dissipate the heat by making use of whole the holding frame. As a result of this, it is possible to pass a strong electric current through the illuminants so as to obtain a strong luminous intensity and the luminous intensity can be stabilized and the life duration can be elongated. Since a heat conductivity of air is 0.02 kcal/mh deg C. and a heat conductivity of the heat-dissipating member whose main material is silicone, fluorosilicone, SEP or the like is more than about 1 kcal/mh deg C., there turns out to be a big difference between a case without any heat-dissipating member and a case with a heat-dissipating member.

Further, since it is possible for the heat-dissipating member to tightly attach to both the curved illuminant loading face and the supporting face of the holding frame with ease because of its flexibility and elasticity, manufacturing and assembling process can be simplified.

In addition, since the heat-dissipating member tightly attaches to the illuminant loading face and the holding frame, a chance of the illuminant loading member getting loose will be reduced, which keeps a condition of the loaded illuminant in an improved state, thereby to contribute improvement of the quality of light irradiation.

A meaning of "tabular" includes a state in which a thickness differs partially.

If a portion where a lead wire of the illuminant, a resistance or the like usually projects out from the back side of the illuminant loading face and the heat-dissipating member is prevented from tightly attaching to the back side, namely at least a surface of the heat-dissipating member is so flexible that it can tightly attach to the back face of the illuminant loading face by transforming itself to dent so as to wrap around a lead wire of the illuminant or an electronic component projecting out from the back side of the illuminant loading face, the above-mentioned problems can be solved and effects of the present claimed invention can sufficiently be produced.

If flexibility of elasticity of the heat-dissipating member is too big, the heat-dissipating member cannot keep its shape in an ordinary condition and an assembling process of engaging might be enmeshed, a problem also might occur such that the heat dissipating plate is shredded or fails to be peeled off on an occasion of exchanging. In order to prevent the problem, it is preferable that the heat-dissipating member has a characteristic of keeping its shape when placed on a flat surface and also it is preferable that the a flexibility of the heat-dissipating member is such a degree that the heat-dissipating member can be peeled off from the illuminant loading member and the holding frame.

As a concrete hardness to obtain the above-mentioned effects, it is preferable that a surface of the heat-dissipating member is no fewer than 10 degrees and no more than 30 degrees in an Asker C hardness that indicates flexibility.

As a concrete embodiment for contributing to simplifying a manufacturing process it is preferable that the illuminant loading member is a print substrate that has a toric shape having a cutout at a part thereof and that can be curved along a direction of its thickness, one face of the print substrate is set as the illuminant loading face, the illuminant loading face is formed to be a concave face of a cone frustum shape by jointing or proximately holding one side of the cutout of the illuminant loading member and the other side of the cutout so that the illuminant loading face locates in the concave face.

As another embodiment of the present claimed invention represented is a lighting unit and a method for manufacturing a lighting unit characterized by that a print substrate that is in a toric shape having a cutout at a part thereof that can be curved along a direction of its thickness is held in a tabular state or in a generally tabular state, a plurality of illuminants are loaded on an illuminant loading face set on one of the faces thereof and then one side of the cutout and the other side of the cutout are jointed or proximately held to make the print substrate in a shape of a cone frustum so that the illuminant loading face locates in a concave face side of the cone frustum, or that one side of the cutout of the print substrate and the other side of the cutout are jointed or proximately held to make the print substrate in a shape of a cone frustum so that the illuminant loading face locates in a concave face side of the cone frustum and then a plurality of illuminants are loaded on the illuminant loading face, and in the meanwhile a heat-dissipating member that is in a same shape or in a generally same shape in a plane view as that of the print substrate and that can be curved along a direction of its thickness is formed to be in a shape of a cone frustum by jointing or proximately holding one side of a cutout provided on the heat-dissipating member and the other side of the cutout and a contact face arranged at a concave face side of the heat-dissipating member is tightly attached to a back face of the illuminant loading face of the print substrate.

In accordance with the arrangement, since it is possible to form the concave face of the cone frustum that can tightly attach to the back face of the illuminant loading face just by jointing or proximately holding one side of the cutout of the heat-dissipating member and other side of the cutout, heat can be dissipated with ease from the illuminants arranged on the curved concave face. As a result of this, the temperature of the illuminants can be lowered effectively by dissipating the heat from the illuminants, thereby to suppress temperature rise of the illuminants. Resultingly high luminous intensity can be obtained and life duration of the lighting unit can be extended.

In addition, there is no need of arranging a hole for implanting the illuminants on a holding frame and the illuminants and wiring can be provided on the concave face of the cone frustum shape with ease, thereby to simplify a manufacturing method. Further, it becomes possible to form a variety of cone frustum shapes with ease by varying a size of the cutout or a diameter of the heat-dissipating member or the print substrate.

As another embodiment to produce the same effects as the above represented is that a heat-dissipating member that is in a same shape or in a generally same shape in a plane view as that of a print substrate and that can be curved along a direction of its thickness is tightly attached or generally tightly attached to a back face of a illuminant loading face of the print substrate and one side of the cutout of the print substrate on which the illuminants and the heat-dissipating member are loaded and the other side of the cutout are jointed or proximately held to form a shape of a cone frustum so that the illuminant loading face locates in a concave side.

As a preferable embodiment to improve a heat-dissipating characteristic represented is a lighting unit wherein a plurality of illuminants are arranged on a curved illuminant loading face provided on a holding frame and a heat-dissipating member that can be curved along a direction of its thickness is tightly attached to a back face of the illuminant loading face and the holding frame. In accordance with the arrangement, it is possible to transmit heat generated from the illuminants effectively and quickly to the holding frame through the heat-dissipating member, thereby to dissipate the heat by making use of whole the holding frame. Since a heat conductivity of air is 0.02 kcal/mh deg C. and a heat conductivity of the heat-dissipating member whose main material is silicone, fluorosilicone, SEP or the like is more than about 0.8 kcal/mh deg C., there turns out to be a big difference between a case without any heat-dissipating member and a case with a heat-dissipating member. Further, another effect is also obtained that the print substrate can be prevented from transformation or being shaky due to the heat dissipating plate.

In order to contribute to improvement of a degree of attaching or a heat-dissipating characteristic and to contribute to simplifying a manufacturing process as well, it is preferable that a face of the heat-dissipating member that tightly attaches to the back face of the illuminant loading face is flexible. "Flexible" here means so soft that the face is transformed to dent so as to wrap around a component such as a resistance arranged on the back face or a projecting lead wire of the illuminants and attaches to the back face of the illuminant loading face when the heat-dissipating member is mounted.

As a further different embodiment, represented is a lighting unit wherein a toric print substrate that can be curved along a direction of its thickness and that has a cutout at a part thereof is held in a tabular state and with this condition kept a plurality of illuminants are loaded on an illuminant loading face set on one of the faces thereof, one side of the cutout and the other side of the cutout are jointed or proximately held so that the illuminant loading face locates in a concave side, the print substrate is held by a holding frame, and then a heat-dissipating member is filled or generally filled into a space formed between the back face of the illuminant loading face and the holding frame. "Filled or generally filled" here means a state in which the heat-dissipating member bridges the abovementioned space so as to tightly attach to both the back face of the illuminant loading face and the holding frame.

A lighting unit wherein a plurality of illuminants are arranged on an illuminant loading face that is provided on a holding frame and that is in a shape of a curved concave face may be so arranged that a heat-dissipating member that is liquid or gelled at least at a time to fill the heat-dissipating member is filled or generally filled in a space formed on a back face of the illuminant loading face.

BRIEF DESCRIPTION OF THE DRAWINGS

FIG. 23 is a central longitudinal cross-sectional view of a conventional lighting system.

DETAILED DESCRIPTION OF THE PREFERRED EMBODIMENTS

Figure 1:
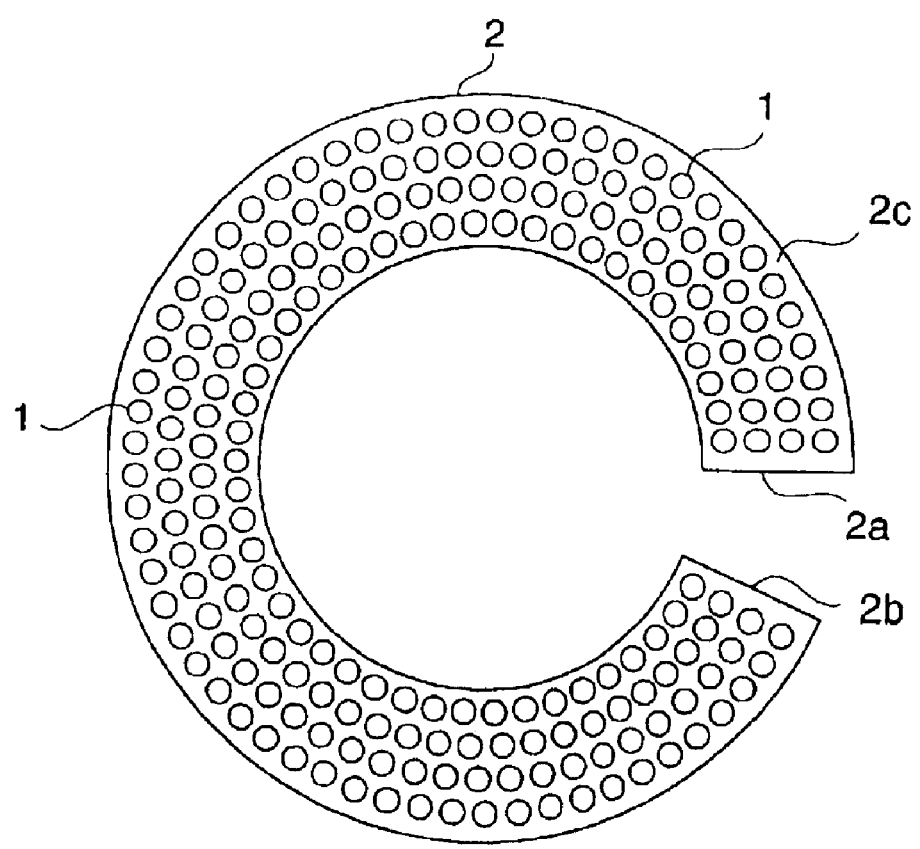
FIG. 1 is a plane view showing a tabular state of a print substrate loaded with LEDs in accordance with one embodiment of the present claimed invention.
Figure 2:
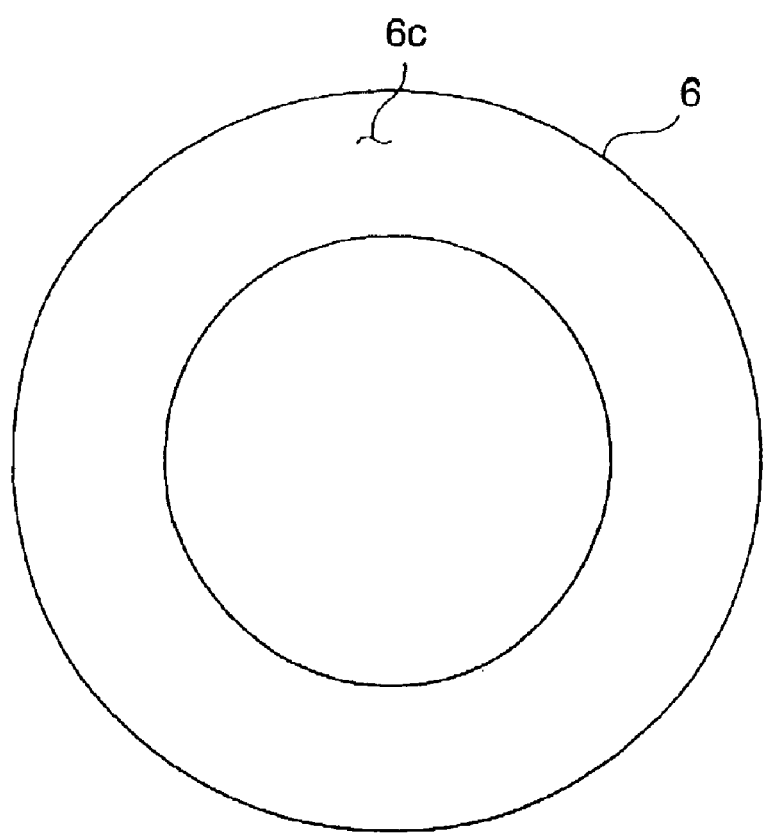
FIG. 2 is a plane view showing a tabular state of a heat dissipating plate in accordance with the embodiment.
Figure 3:
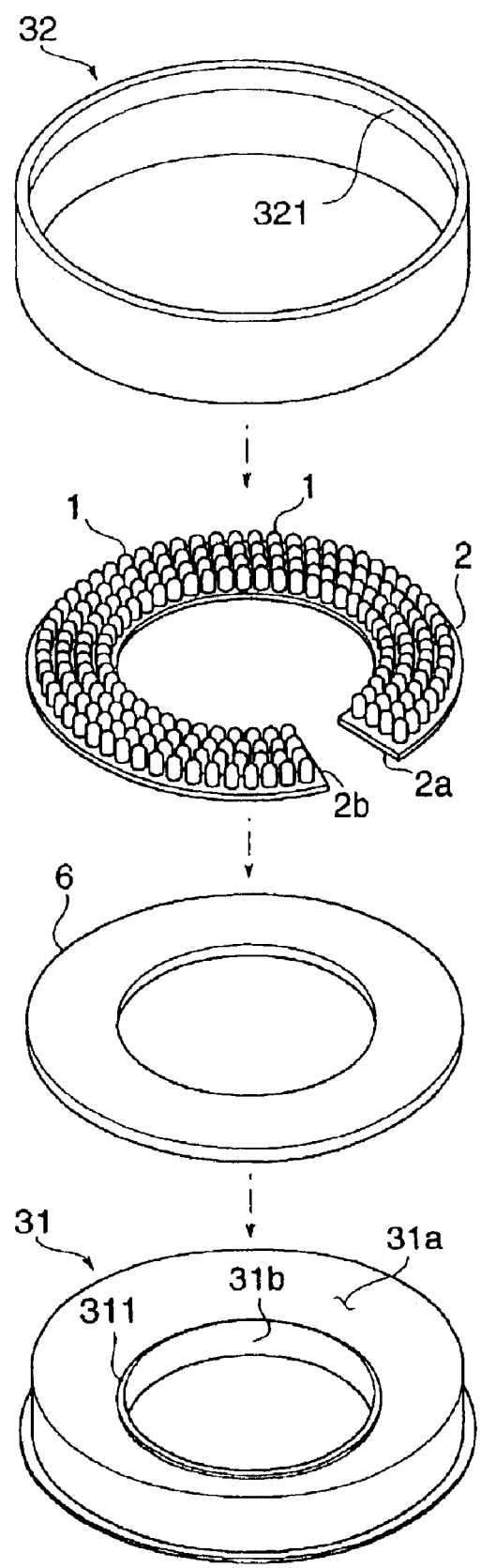
FIG. 3 is an exploded perspective view of the light irradiating unit in accordance with the embodiment.
Figure 4:
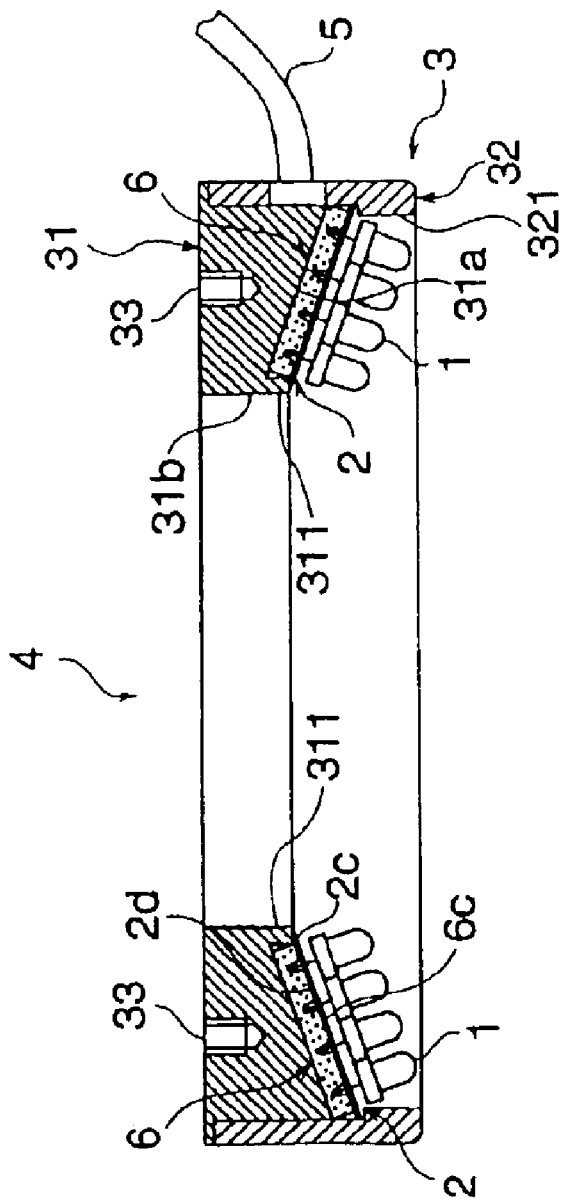
FIG. 4 is a central longitudinal cross-sectional view of the light irradiating unit in accordance with the embodiment.

A first embodiment of the present claimed invention will be described with reference to the drawings.

A light irradiating unit 4 in accordance with the embodiment comprises, as shown in FIG. 1 through FIG. 4, LEDs 1 as a plurality of illuminants, a print substrate 2 that has a toric shape having a cutout at a part thereof and that can be curved along a direction of its thickness, a heat dissipating plate 6 as a heat-dissipating member that has a toric shape and that is flexible and a case 3 as a holding frame that has a center hole 31b for visual inspection or filming and that holds the print substrate 2.

More specifically, the LED 1 is a shell-shaped lump type and an element of the LED 1 is covered with a shell-shaped transparent resin mold having a lens effect. It is a matter of course that the LED 1 may be a chip-type.

The print substrate 2 is flexible hierarchical structure of a cover material, a copper foil and a base material or the like and wiring of the LEDs 1 is printed beforehand.

The heat dissipating plate 6 is in a toric shape made of silicone, fluorosilicone, SEP or the like as a main material and is electrically insulated, high in heat conduction, elastic and flexible. When the heat dissipating plate 6 is tightly attached to a back face 2d of the print substrate 2, the contact face 6c of the heat dissipating plate 6 is transformed to dent so as to wrap around a component such as a resistance arranged on the back face 2d or a projecting lead wire of the LEDs 1. The heat dissipating plate 6 is made of a material having a characteristic of keeping its shape when placed on a flat surface. More specifically, the material of the heat dissipating plate 6 is no fewer than 10 degrees and no more than 30 degrees in an Asker C hardness that indicates flexibility. If the material is too hard, a degree of attaching the heat dissipating plate 6 to the back face 2d of the print substrate 2 might be lowered due to failure of absorbing concavity or convexity such as a resistance or the like. If the material is too soft, a problem might occur such that the heat dissipating plate 6 fails to keep its shape or it is shredded or fails to be peeled on an occasion of exchanging. Generally silicone rubber (a material of the heat dissipating plate 6 used in this embodiment) includes low molecular weight siloxane and the low molecular weight siloxane (namely, an oily ingredient) bleeds (exudes soakingly) on the surface of the heat dissipating plate 6 if the heat dissipating plate 6 is arranged between the print substrate 2 and the case 3 for a long time. The low molecular weight siloxane bleeds just by being pressed. All the more because the temperature of the print substrate 2 rises when the LEDs 1 are turned on electricity to illuminate, a phenomenon of bleeding is more accelerated. In this embodiment content of the low molecular weight siloxane is not more than 300 ppm. Silicone rubber usually includes about 3000 ppm of the low molecular weight siloxane and has the above-mentioned problem.

The case 3 comprises a cylinder case body 31 that is in a certain degree of thickness and that has a center hole 31b for monitoring a subject to be irradiated from an opposite side of the subject and a cylinder holding member 32 that fits over a periphery of the case body 31. At an end of the case body 31 provided is a concave face 31a of a cone frustum whose center is most dented and the concave face 31a serves as a supporting face that faces to the back face 2d of the print substrate 2. An inclining angle of the concave face 31 of the cone frustum is the same or generally the same as that of the back face 2d of the print substrate 2 which is made to be a shape of a cone frustum by jointing or proximately holding one side 2a of the cutout and the other side 2b of the cutout of the print substrate 2.

One end portion of the holding member 32 provided is a protruding portion 321 protruding inward and the protruding portion 321 serves as a stem to prevent the print substrate 2 mounted on the case body 31 from dropping out. A female screw 33 bored in the case body 31 is for mounting the light irradiating unit 4.

With this arrangement, a method for assembling the light irradiating unit 4 in accordance with the embodiment will be explained. First, the print substrate 2 is held in a tabular state and a plurality of LEDs 1 are implanted in all over an illuminant loading face 2c as one of the faces of the print substrate 2 with soldering or the like. Then one side 2a of the cutout and the other side 2b of the cutout of the print substrate 2 are jointed or proximately held so as to locate the illuminant loading face 2c in a concave face side. Consequentially the print substrate 2 is formed to be a shape of a cone frustum and the illuminant loading face 2c is a concave face of the cone frustum on which the LEDs 1 are arranged. A power cable 5 is also wired on the print substrate 2 with soldering or the like.

Next, the heat dissipating plate 6 is pasted to the supporting face 31a of the case body 31. At this time the heat dissipating plate 6 transforms itself by making use of its characteristic of elasticity and one face of the heat dissipating plate 6 tightly attaches to the supporting face 31a.

Then one side 2a of the cutout and the other side 2b of the cutout of the print substrate 2 are jointed or proximately held so as to attach the back face 2d of the print substrate 2 to other face of the heat dissipating plate 6 in a process of forming the print substrate 2 to be a shape of a cone frustum. It is a matter of course that the heat dissipating plate 6 may first be pasted to the back face 2d of the print substrate 2 and then the print substrate 2 with the heat dissipating plate 6 pasted may be tightly attached to the supporting face 31a. A meaning of "tightly attach" includes a part of a face tightly attaches to a part of another face.

A projecting portion 311 that is arranged at a rim of an opening of the center hole 31b of the case body 31 and that projects toward an axial direction is so set that an external diameter thereof is generally equal to both a diameter of a center hole of the heat dissipating plate 6 and a diameter of a center hole of the print substrate 2 in a shape of the cone frustum and serves as a positioning portion for mounting the heat dissipating plate 6 or the print substrate 2 on the case body 31.

And then the holding member 32 is fixed to the case body 31 by fitting over the case body 31 from a side of the concave face 31a of the cone frustum shape so as to fix the print substrate 2 and to prevent it from dropping out by making the protruding portion 321 an abutting contact with a peripheral end of the print substrate 2.

In accordance with the arrangement, since heat generated by the LEDs 1 is effectively and rapidly transmitted to the case 3 through the heat dissipating plate 6 and the heat can be dissipated from whole of the case 3, the temperature of the LEDs 1 can be lowered effectively by dissipating the heat from the LEDs 1, thereby to suppress temperature rise of the LEDs 1. As a result of this, high luminous intensity of the lighting unit 4 can be obtained and life duration of the lighting unit 4 can be extended.

Further, another effect is also obtained that the print substrate 2 can be prevented from transformation or being shaky due to the heat dissipating plate 6 whose front and back faces have a predetermined softness or a certain degree of viscosity. This contributes to making a direction of the LEDs 1 constant, thereby to increase a degree in concentration of light and to prevent irregularity in luminous intensity at a portion to be irradiated.

In addition, since the heat dissipating plate 6 is flexible and elastic and can be tightly attached to both the back face 2c of the curbed illuminant loading face 2c and the supporting face 31a of the case 3 with ease, a process of manufacturing the lighting unit 4 is not complicated. Especially in accordance with this embodiment, since the curved illuminant loading face 2c can be formed just by jointing or proximately holding one side 2a of the cutout and the other side 2b of the cutout of the print substrate 2, an assembling process is simple and a process of manufacturing the lighting unit 4 is not complicated.

Figure 5:
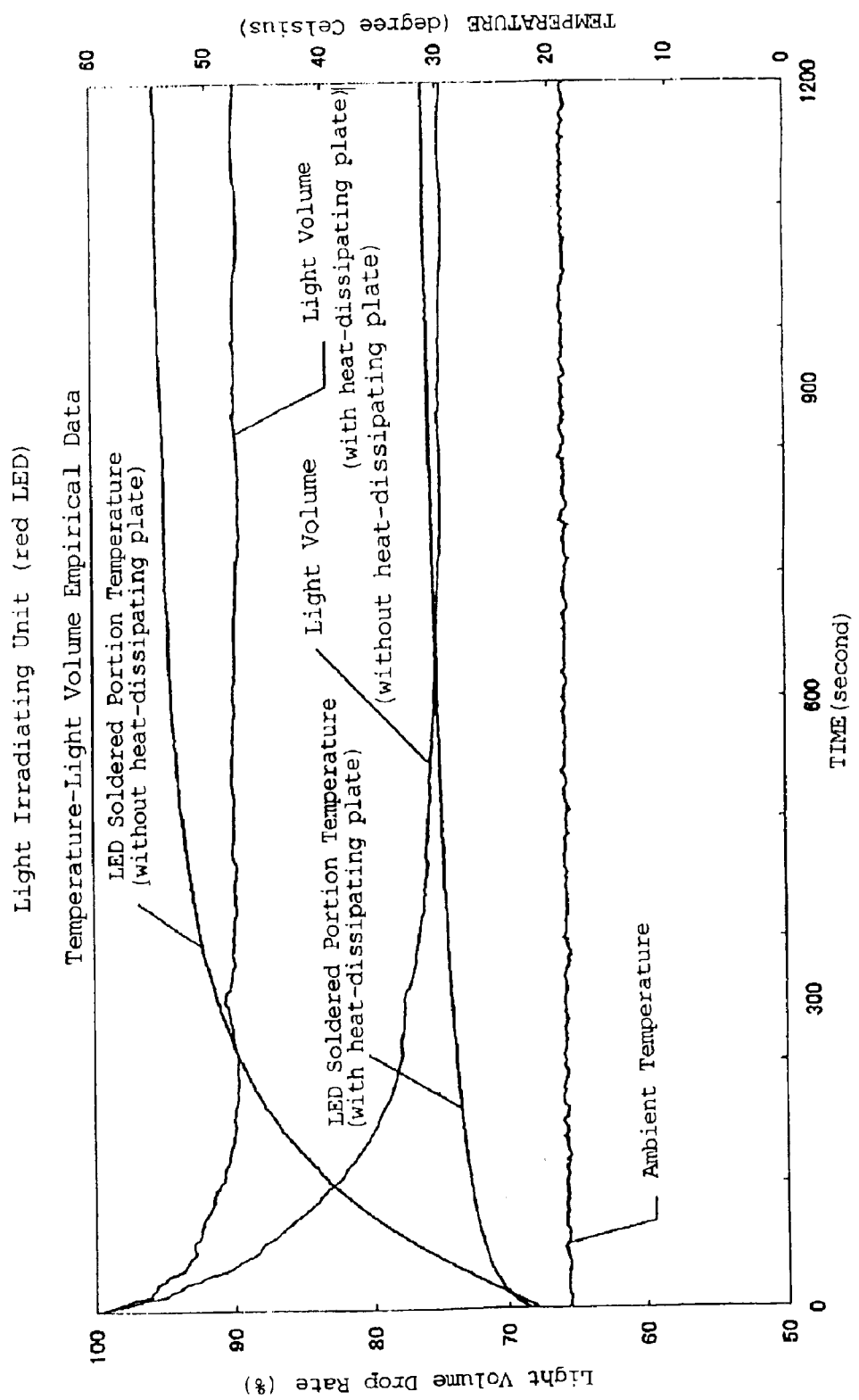
FIG. 5 is a temperature empirical data (red LEDs) showing an effect of the present claimed invention.
Figure 6:
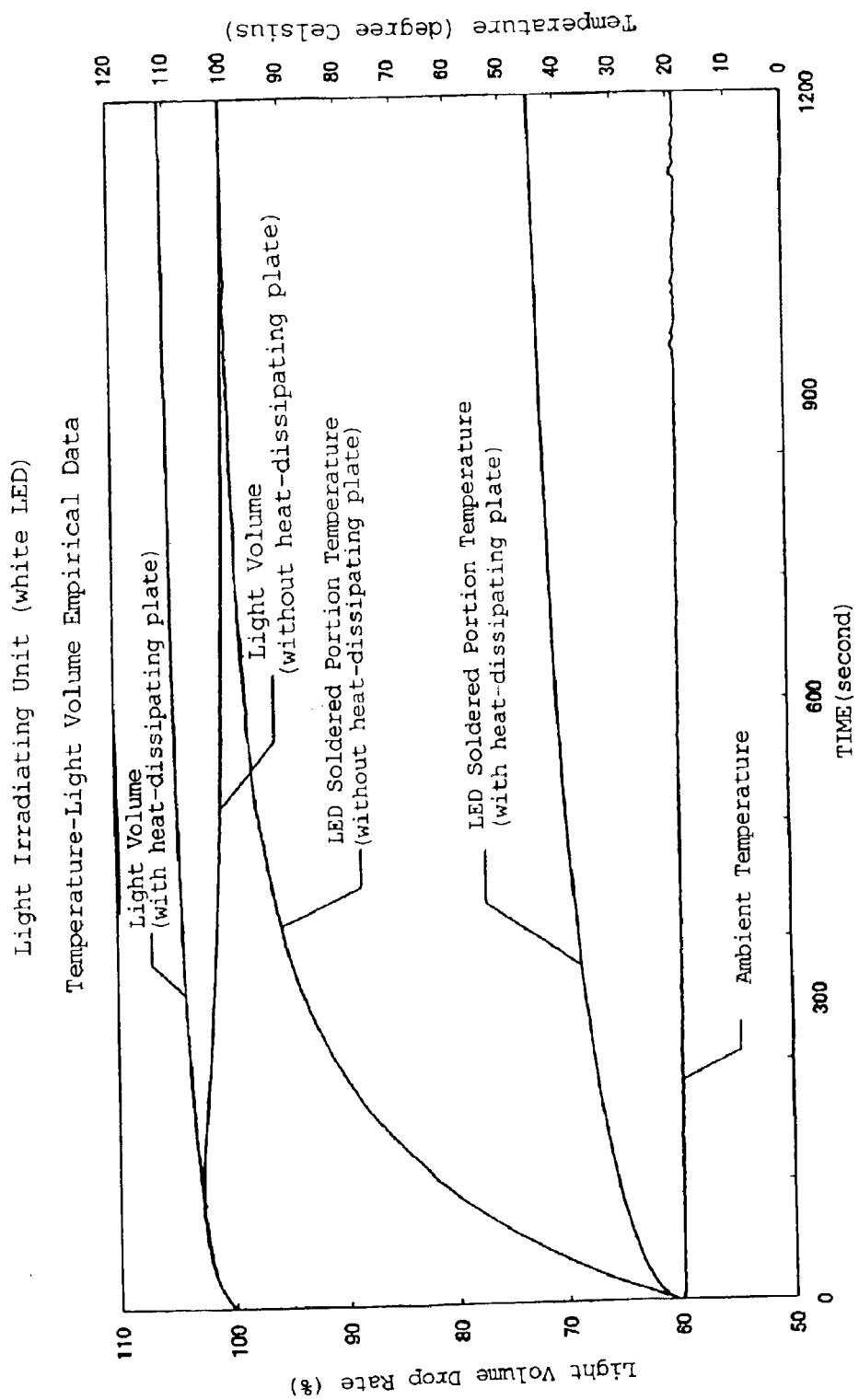
FIG. 6 is a temperature empirical data (white LEDs) showing an effect of the present claimed invention.
Figure 7:
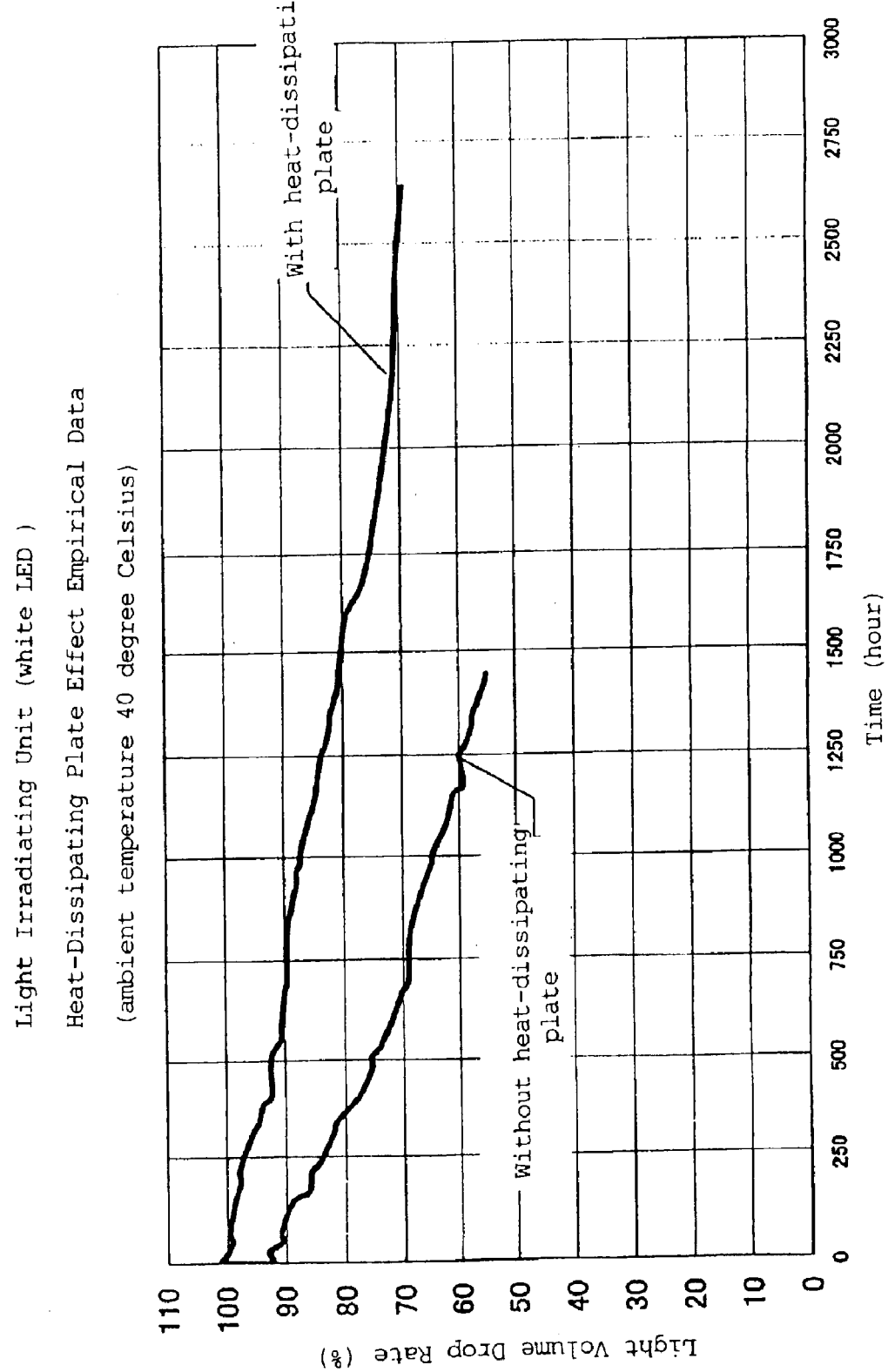
FIG. 7 is a deterioration empirical date (white LEDs) showing an effect of the present claimed invention.

Concrete effect will be shown in FIG. 5, FIG. 6 and FIG. 7.

FIG. 5 and FIG. 6 show an empirical data of a comparative experiment showing a drop degree of a light volume in a short term (20 minutes) with and without the heat dissipating plate 6. FIG. 5 is an empirical data of the red LEDs. As shown in FIG. 5, a temperature of a soldered portion of the LEDs 1 differs about 25 degree Celsius from the case with the heat dissipating plate 6 to the case without the heat dissipating plate 6. Light volume shows a distinguishing difference that the light volume after 20 minutes drops about 10% compared with an initial light volume in the case with the heat dissipating plate 6 while the light volume after 20 minutes drops about no less than 25% compared with an initial light volume in the case without the heat dissipating plate 6. FIG. 6 shows an empirical data of a comparative experiment in case of the white LEDs with and without the heat dissipating plate 6. In this experiment, without the heat dissipating plate 6 a temperature of a soldered portion of the LEDs 1 rises up to 100 degree Celsius that is a limit of a proper operational temperature of the LEDs 1. This originates in that a forward voltage (VF) of the white LEDs, blue LEDs and green LEDs is as high as 3.5 V and a heat release value tends to be big. Without the heat dissipating plate 6, the LEDs might be deteriorated due to a high temperature depending on a service condition, resulting in a great influence on a life duration and luminous intensity. By contrast with the above case, the temperature is kept at around 45 degree Celsius with the heat dissipating plate 6. Accordingly a temperature difference is turned out to be no less than 55 degree Celsius.

FIG. 7 shows an empirical data of a comparative experiment showing a degree of deterioration of white LEDs after a long term use with and without the heat dissipating plate 6. The light volume drops to a half in 1500 hours after an initiation of the experiment for a case without the heat dissipating plate 6 and a quality of the LEDs 1 reaches a limit such as the print substrate 2 is burned. On the contrary, the light volume declines only 20 percent in 1500 hours after an initiation of the experiment for a case with the heat dissipating plate 6 and later the light volume declines little by little. In spite of the decline in light volume, the LEDs are sustainable for use for another long time. More specifically, with or without the heat dissipating plate 6 has a great influence on the light volume and duration of life.

The experiments shown in FIG. 5 and FIG. 6 are the comparative experiment showing a drop degree of a light volume due to high temperature then the LEDs 1 restore the initial light volume when the temperature of the LEDs 1 drop. On the contrary, the experiment shown in FIG. 7 is the deterioration experiment then once the LEDs 1 are deteriorated, the LEDs 1 never restore the initial light volume.

It is a matter of course that there is no need of arranging a hole for implanting the LEDs in a side of the case 3, and another effect of simplifying a manufacturing process can be produced such that the LEDs 1 and wiring also can be provided on the concave face 2c of the cone frustum with ease.

Figure 8:
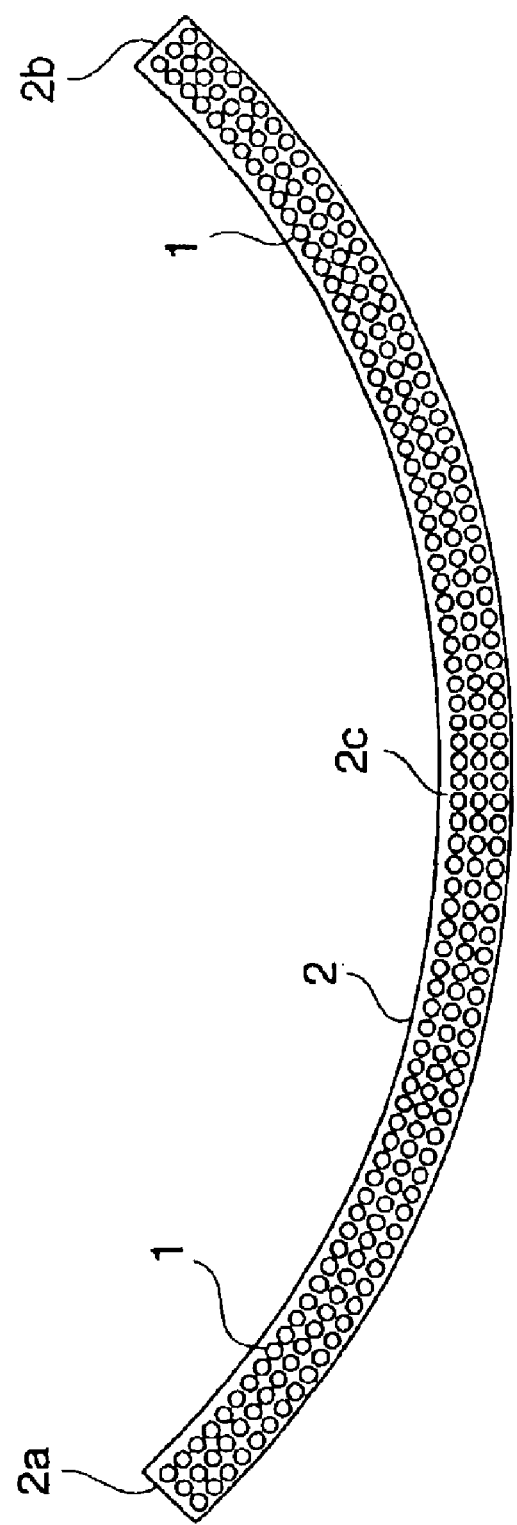
FIG. 8 is a plane view showing a tabular state of a print substrate loaded with LEDs in accordance with a modified form of the embodiment.
Figure 9:
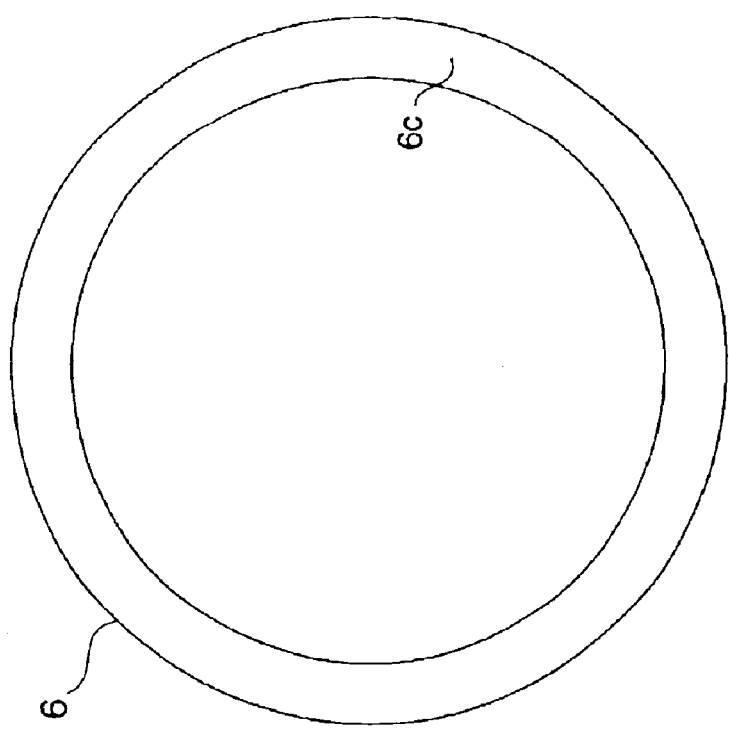
FIG. 9 is a plane view showing a tabular state of a heat dissipating plate in accordance with the modified form.
Figure 10:
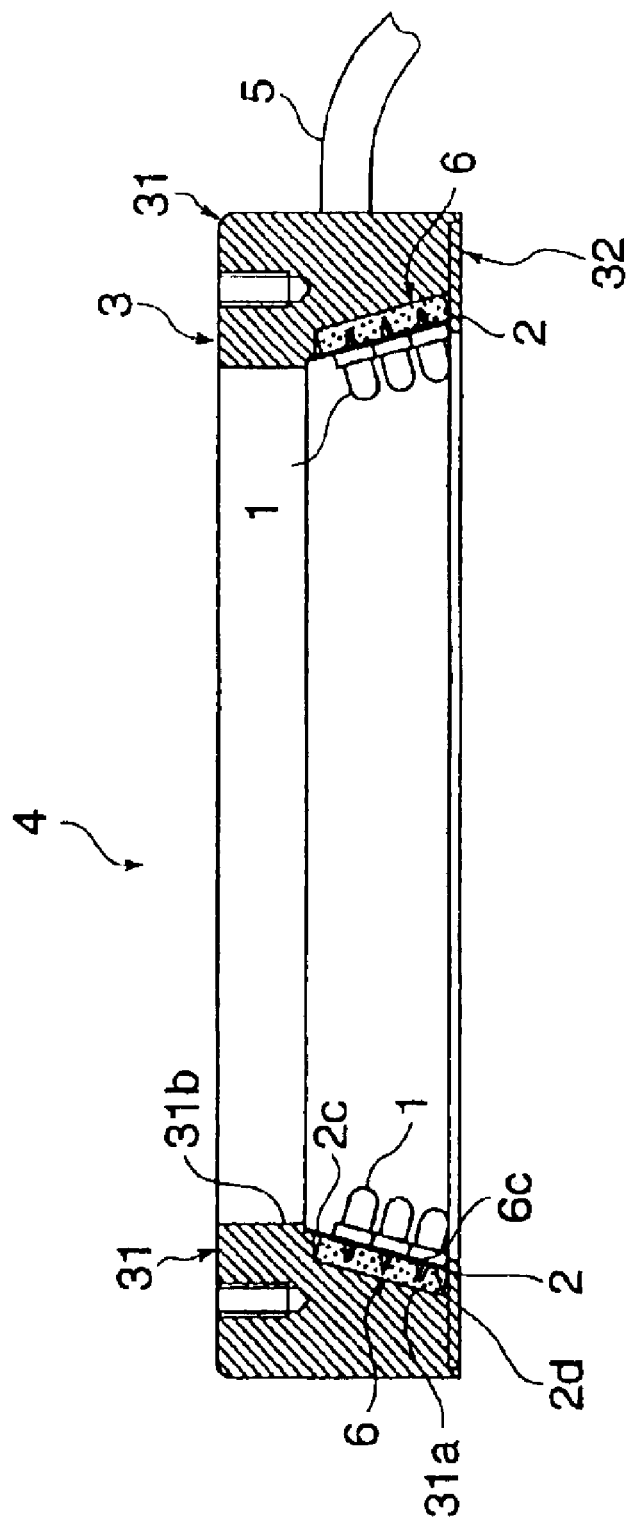
FIG. 10 is a central longitudinal cross-sectional view of a light irradiating unit in accordance with the modified form.

Further, as shown in FIG. 8 through FIG. 10, it becomes possible to form a variety of cone frustum shapes with ease by appropriately varying a size of the cutout or a diameter of the heat dissipating plate 6 or the print substrate 2.

The present claimed invention may be variously varied. In the following explanation of a second and a third embodiments, the component corresponding to the above embodiment will be given the same code.

Figure 11:
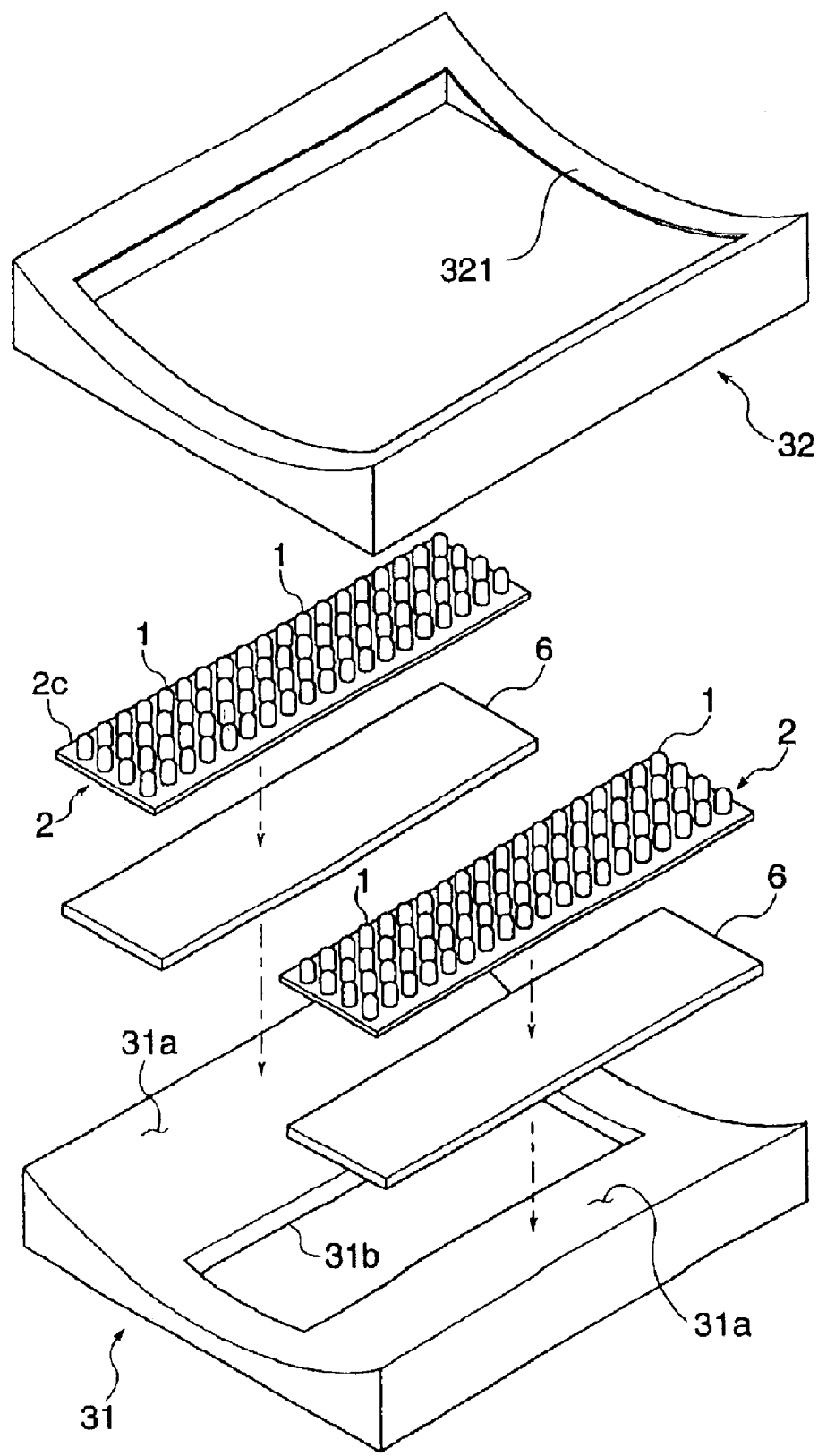
FIG. 11 is an exploded perspective view of a light irradiating unit in accordance with a second embodiment of the present claimed invention.

For example, the illuminant loading face is not limited to the concave face of the cone frustum, but may be any curved face not only a concave or a convex. For example, as shown in FIG. 11, the illuminant loading face 2c may be a concave face of a cylinder. This case is effective for a line inspection.

FIG. 11 shows a case in which two pieces of print substrates 2 and two heat dissipating plates 6 are mounted on the supporting face 31a, but the print substrate and the heat dissipating plate may be divided into more pieces and a plurality of print substrates or heat dissipating plates may be mounted.

Figure 12:
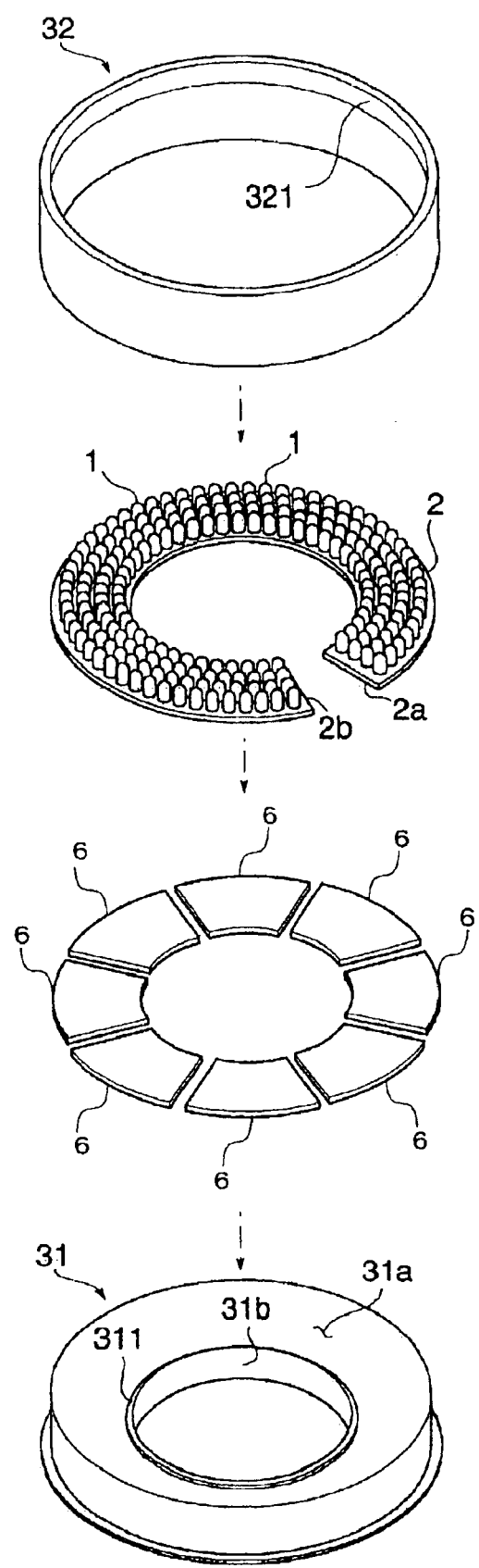
FIG. 12 is an exploded perspective view of a light irradiating unit in accordance with a third embodiment of the present claimed invention.
Figure 13:
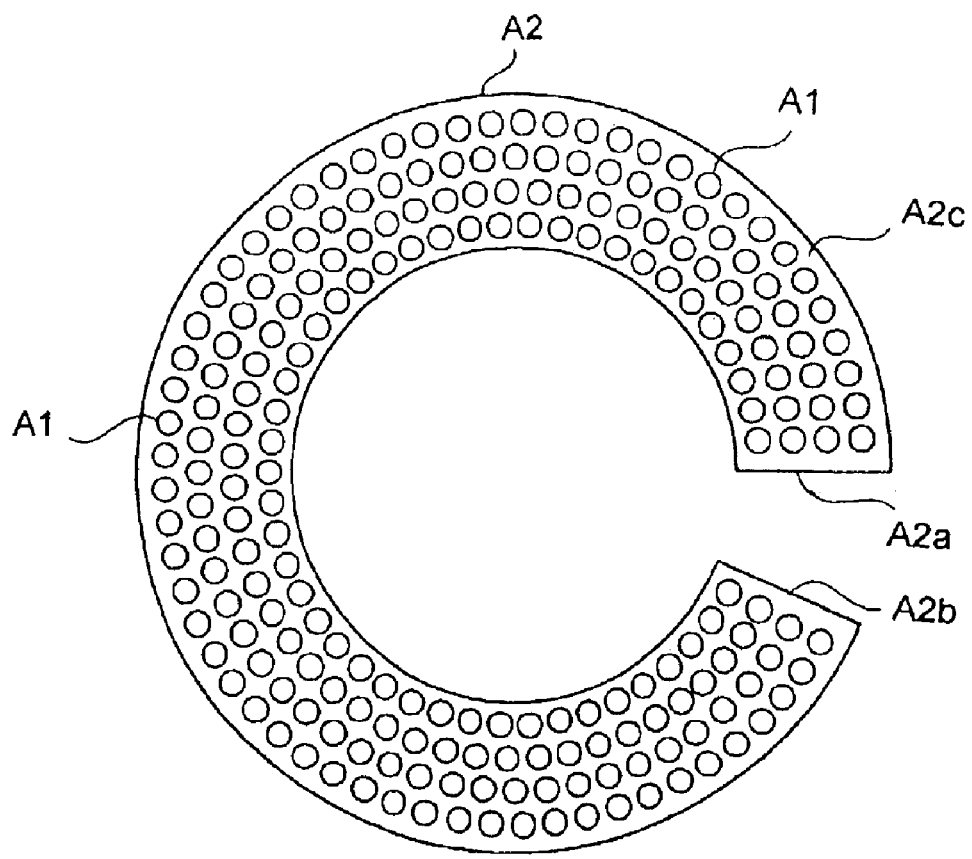
FIG. 13 is a plane view showing a tabular state of a print substrate loaded with LEDs in accordance with a forth embodiment of the present claimed invention.
Figure 14:
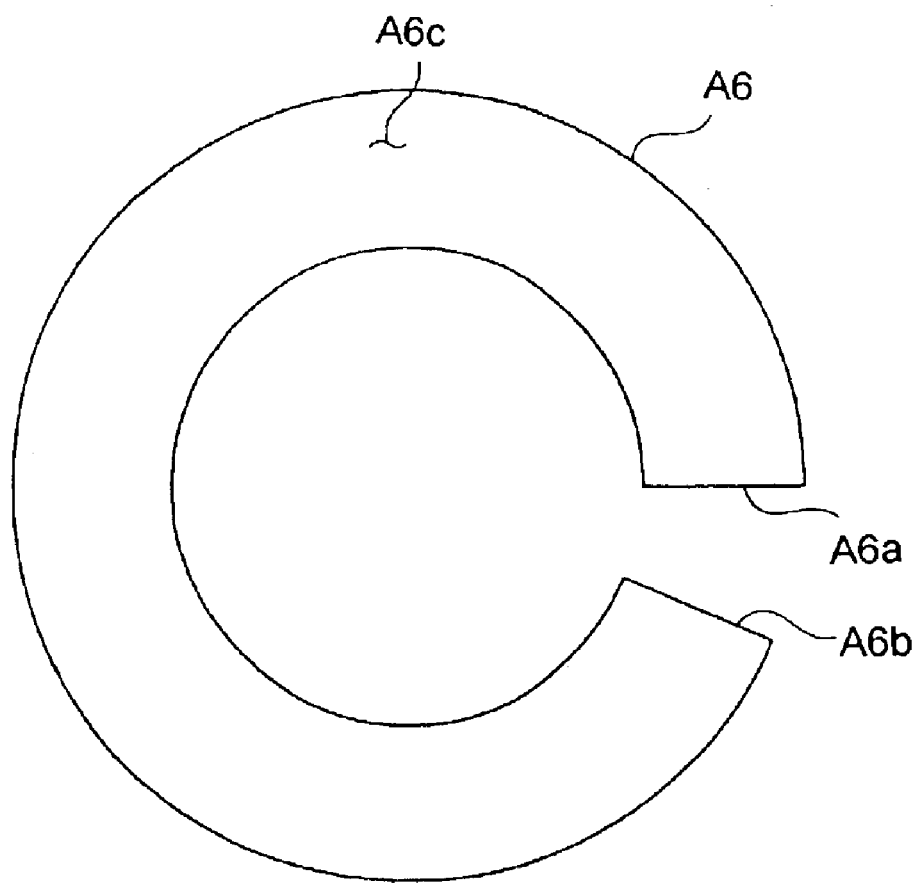
FIG. 14 is a plane view showing a tabular state of a heat dissipating plate in accordance with the embodiment.
Figure 15:
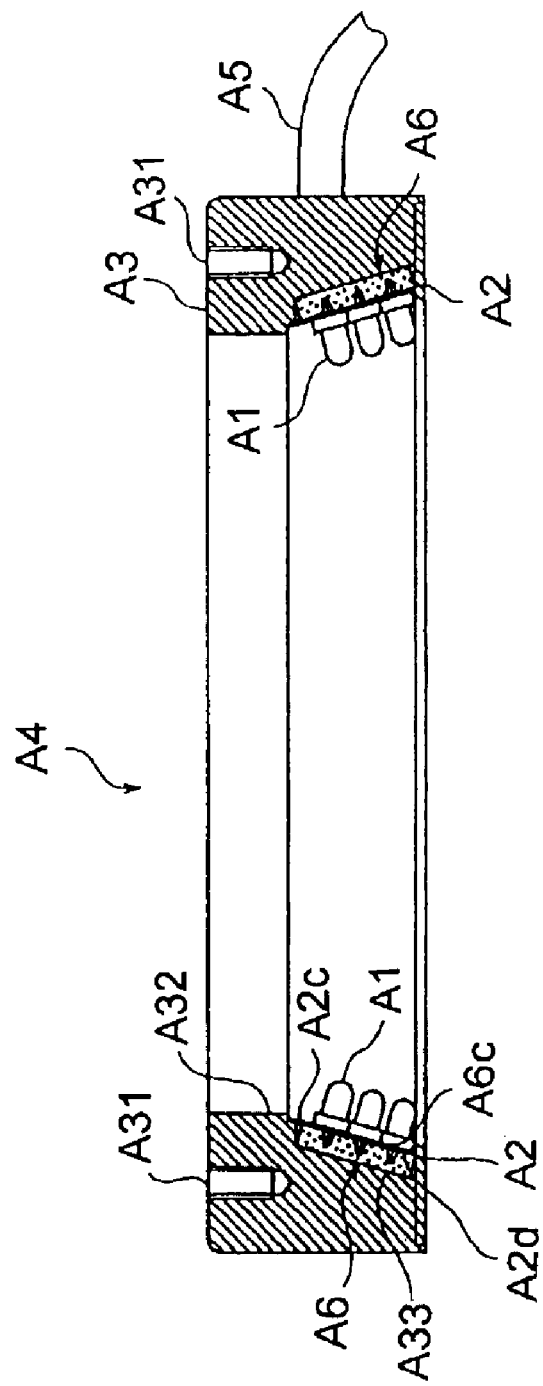
FIG. 15 is a central longitudinal cross-sectional view of a lighting system in accordance with the embodiment.

As shown in FIG. 12 as a third embodiment, the heat-dissipating plate 6 may comprise a plurality of partial toric shapes that is formed to divide a toric shape. In accordance with the arrangement, it is not difficult to attach the heat-dissipating plate 6 to the supporting face 31a of the case body 31 although the heat-dissipating plate 6 may be of a relatively hard material. A degree of freedom to choose a material of the heat-dissipating member 6 can be increased. In addition, the heat-dissipating member 6 is hard to be distorted or deformed when to attach, thereby to make it easy to attach the heat-dissipating member 6. In FIG. 12 each of the heat-dissipating members 6 has the same shape, but may have a different shape. In order to obtain a high heat dissipation effect, it is preferable that each of the heat-dissipating plates 6 is tightly attached to the back face of the print substrate 2 with no space between the adjacent heat-dissipating members 6 so as to cover whole of the back face of the print substrate 2, but may be permitted if a part of the heat-dissipating members 6 are overlapped or there is a small gap between an edge of the heat-dissipating members 6.

In the above embodiment, since the supporting face 31a of the case body 31 is set to be generally parallel to the back face 2d of the illuminant loading face 2c, the heat dissipating plate 6 is in equal thickness. In case that the supporting face 31a is not generally parallel to the back face 2d of the illuminant loading face 2c or in order to cover a case that there is a concave or a convex in a part of the supporting face 31a or the back face 2d, it is preferable that a thickness of the heat dissipating plate 6 varies with tailored to needs.

It is a matter of course that the illuminant loading member does not have to be a flexible print substrate and the light irradiating unit may be used for other purpose than a lighting unit for inspection. In this case, there is no need of arranging a center hole for monitoring on the case body.

In addition, the print substrate may be first curved to be a shape of the cone frustum and then LEDs may be mounted on the concave face of the cone frustum.

Further, a plurality of slits extending toward a radial direction may be intermittently arranged on a periphery of the print substrate. In accordance with the arrangement, it is possible to curve the print substrate with ease.

In addition a wire of the print substrate thicker than a wire usually required for an electric current may be adopted and an effect of heat dissipation may be produced or promoted by the wire itself. In accordance with the arrangement, the effect of heat dissipation can be further increased. More concretely, from an effective heat dissipation standpoint, it is preferable that a width of the wiring connected with a lead wire of the LEDs is made wider.

A forth embodiment of the present claimed invention will be described with reference to the drawings. Codes in this embodiment are not in common with those in the first, second and third embodiments.

A lighting unit A4 in accordance with the embodiment comprises, as shown in FIG. 13 through FIG. 16, LEDs A1 as a plurality of illuminants, a print substrate A2 that is in a toric shape having a cutout at a part thereof and that can be curved along a direction of its thickness, a heat-dissipating plate A6 as a heat-dissipating member that is in a same shape or in a generally same shape in a plane view as that of the print substrate A2 and that can be curved along a direction of its thickness and a lighting case A3 as a holding frame that has a center hole A32 for visual inspection or filming and that holds the print substrate A2. A female screw A31 arranged on the lighting case A3 is for mounting the lighting unit A4.

With this arrangement, a method for manufacturing the lighting unit in accordance with the embodiment will be explained. First, the print substrate A2 is held in a tabular state and a plurality of LEDs A1 are implanted all over an illuminant loading face A2c set on one of the faces of the print substrate A2 with soldering or the like. Then one side A2a of the cutout of the print substrate A2 and the other side A2b of the cutout are jointed or proximately held so as to locate the illuminant loading face A2c in a concave side. Consequently the print substrate A2 is formed to be in a shape of a cone frustum and the illuminant loading face A2c is in a concave face of the cone frustum on which the LEDs are arranged. A power cable A5 is also wired on the print substrate A2 with soldering.

On the other hand, the heat-dissipating plate A6 is formed to be in a shape of a cone frustum by jointing or proximately holding one side A6a of the cutout of the heat-dissipating plate A6 and the other side A6b of the cutout. Next, a contact face A6c arranged at a concave face of the heat-dissipating plate A6 is tightly attached to a curved back face A2d of the illuminant loading face A2c. A meaning of "tightly attached" here includes a state in which a part or all of the back face A2d is tightly attached to a part or all of the contact face A6c.

The heat-dissipating plate A6 is made of silicone, fluorosilicone, SEP or the like as a main material and is electrically insulated, flexible and high in heat conduction. When the heat-dissipating plate A6 is tightly attached to the back face A2d of the print substrate A2, the contact face A6c is transformed to dent so as to wrap around a component such as a resistance arranged on the back face A2d or a projecting lead wire of the LEDs A1. The contact face A6c may be adhered to the back face A2d with applying pressure-sensitive adhesive or adhesive to the contact face A6c.

Next, the heat-dissipating plate A6 and the print substrate A2 loaded with the LEDs A1 are held by a holding groove A33 that is arranged on the lighting case A3. The holding groove A33 in this embodiment is so big that the print substrate A2 and the heat-dissipating plate A6 can be accommodated. The heat-dissipating plate A6 is fitted into the holding groove A33 and is attached or generally attached to both the back face A2d of the print substrate A2 and a bottom face of the holding groove A33.

In accordance with the arrangement, since heat generated by the LEDs A1 is effectively transmitted to the holding frame A3 speedily and it is possible to dissipate the heat from whole of the holding frame A3, the temperature of the LEDs A1 can be lowered effectively by dissipating the heat from the LEDs A1, thereby to suppress temperature rise of the LEDs A1. As a result of this, high luminous intensity of the lighting unit can be obtained and life duration of the lighting unit A4 can be extended.

Further, if the heat-dissipating plate A6 is arranged between the LEDs A1 and the holding frame A3, another effect is also obtained that the print substrate A2 can be prevented from transformation or being shaky.

In addition, since it is possible to form a shape of a cone frustum that can be tightly attached to the back face 2d of the print substrate A2 just by jointing or proximately holding one side A6a of the cutout and the other side A6b of the cutout of the heat-dissipating plate A6, an assembling is simple and a process of manufacturing the lighting unit A4 is not complicated.

Figure 21:
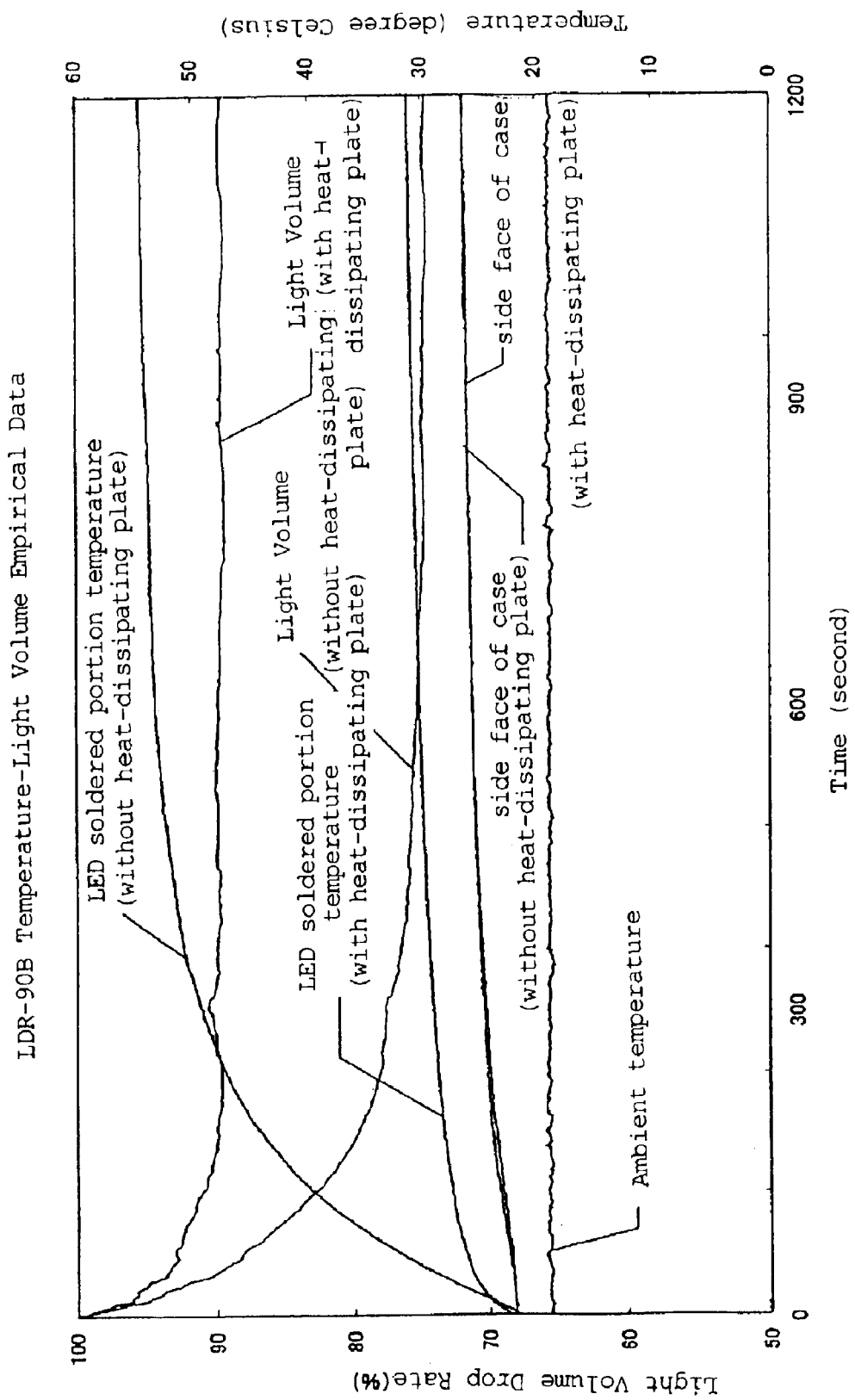
FIG. 21 is an empirical data (red LEDs) showing an effect of the present claimed invention.
Figure 22:
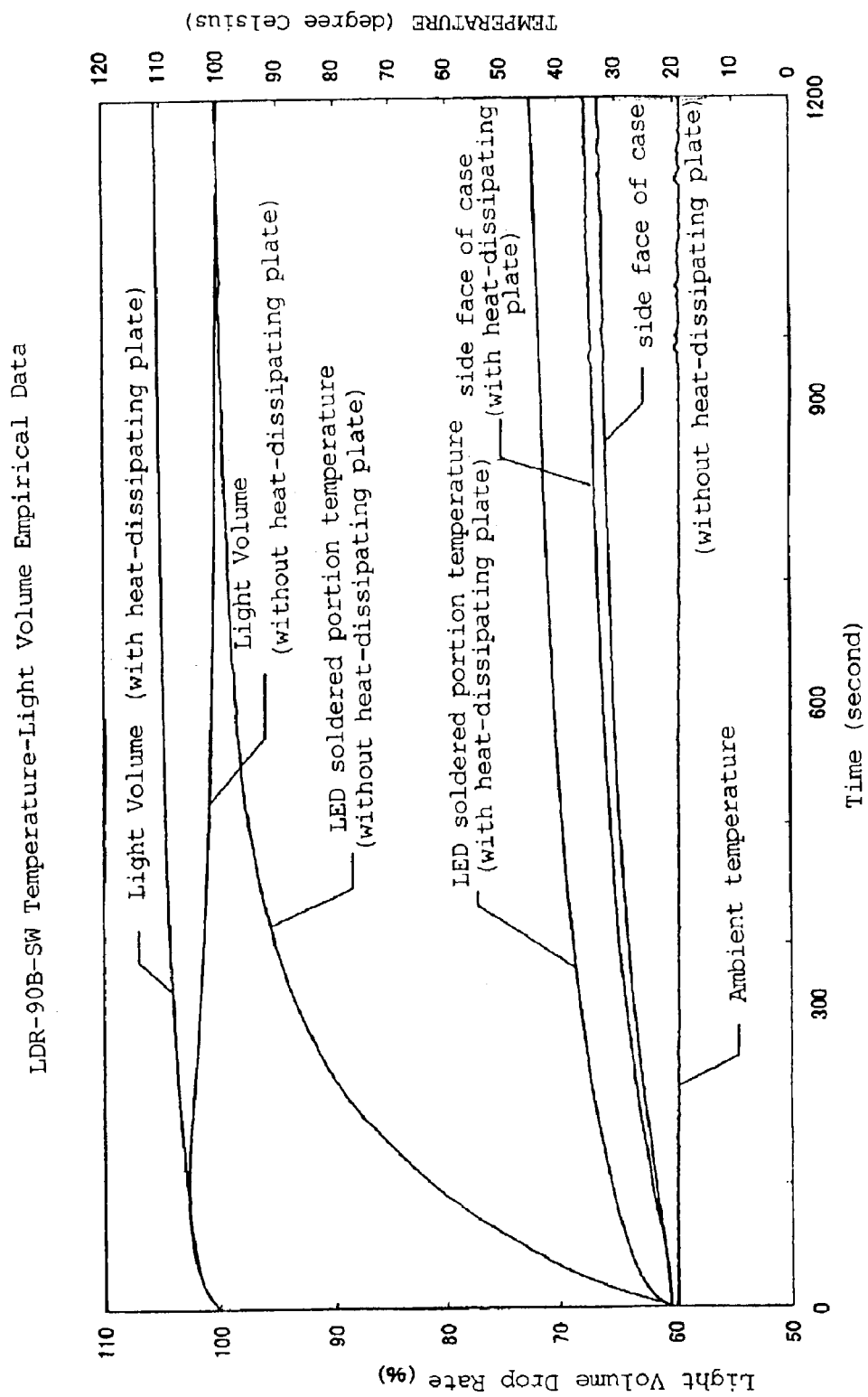
FIG. 22 is an empirical data (white LEDs) showing an effect of the present claimed invention.

Concrete effect will be shown in FIG. 21 and FIG. 22. FIG. 21 shows an empirical data of a comparative experiment in case of the red LEDs with and without the heat-dissipating plate A6. As shown in FIG. 21, 20 minutes after an initiation of the experiment, a temperature of a soldered portion of the LEDs A1 differs about 25 degree Celsius from the case with the heat-dissipating plate A6 to the case without the heat-dissipating plate A6. Light volume shows a distinguished difference that the light volume after 20 minutes drops about 10% compared with an initial light volume in the case with the heat-dissipating plate A6 while the light volume after 20 minutes drops about no less than 25% compared with an initial light volume in the case without the heat-dissipating plate A6.

FIG. 22 shows an empirical data of a comparative experiment in case of the white LEDs with and without the heat-dissipating plate A6. In this experiment, without the heat-dissipating plate A6 a temperature of a soldered portion of the LEDs A1 rises up to 100 degree Celsius that is a limit of a proper operational temperature of the LEDs A1. This originates in that a forward voltage (VFmax) of the white LEDs, blue LEDs and green LEDs is as high as 3.5 V and a heat release value tends to be big. Without the heat-dissipating plate A6, the LEDs might be deteriorated due to a high temperature depending on a service condition, resulting in a great influence on a life duration and luminous intensity. By contrast with the above case, the temperature is kept at around 45 degree Celsius with the heat-dissipating plate A6. Accordingly a temperature difference is turned out to be no less than 55 degree Celsius.

It is a matter of course that there is no need of arranging a hole for implanting the LEDs in a side of the lighting case A3, and another effect of simplifying a manufacturing process can be produced such that the LEDs A1 and wiring also can be arranged on a cone frustum concave face as the illuminant loading face A2c with ease.

Figure 16:
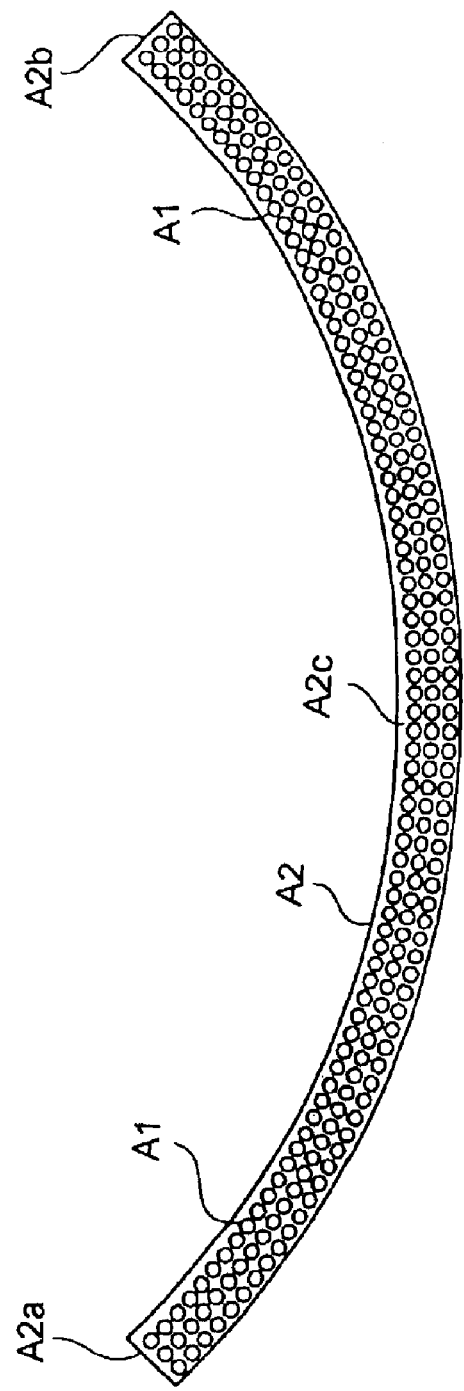
FIG. 16 is a plane view showing a tabular state of a print substrate loaded with LEDs in accordance with a modified form of the embodiment.
Figure 17:
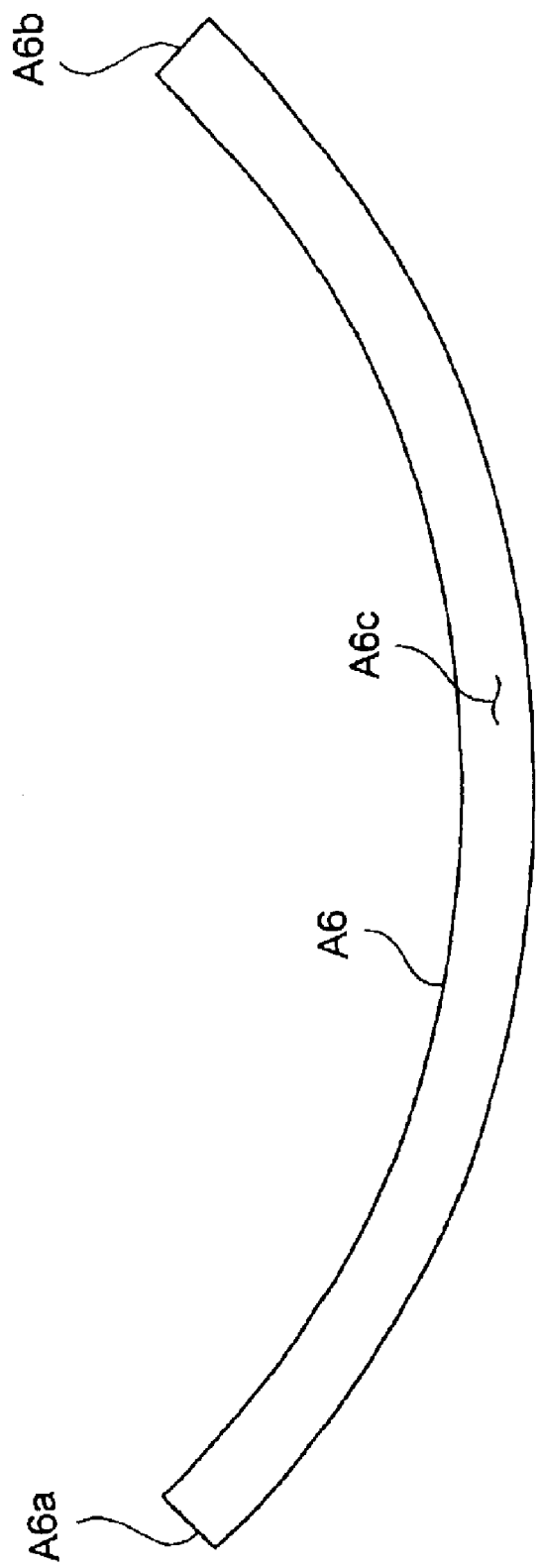
FIG. 17 is a plane view showing a tabular state of a heat-dissipating plate in accordance with the modified form.
Figure 18:
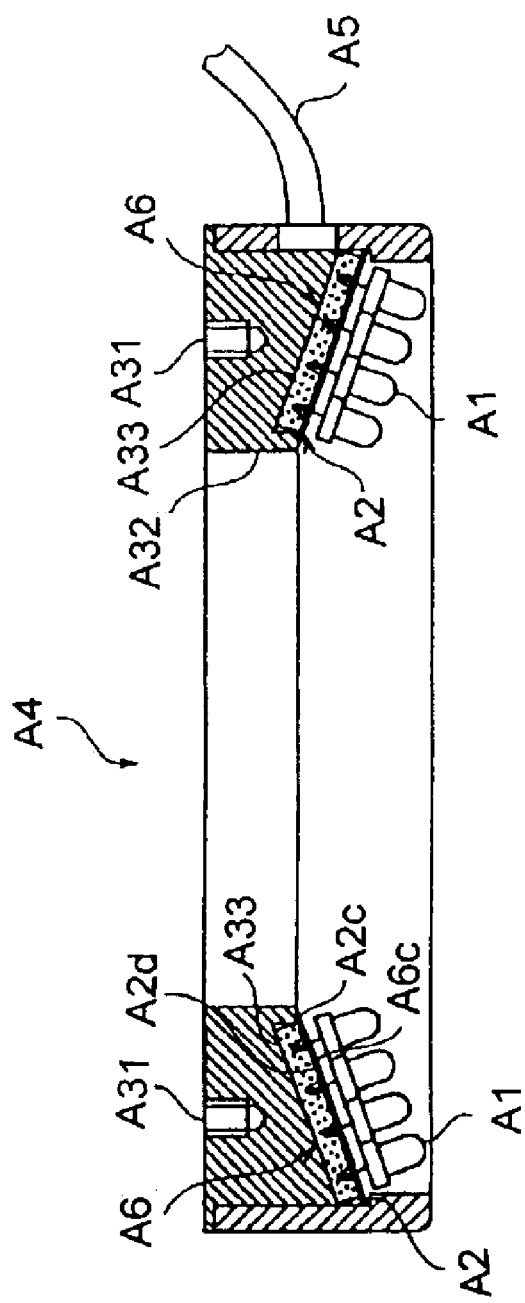
FIG. 18 is a central longitudinal cross-sectional view of a lighting system in accordance with the modified form.

Further, as shown in FIG. 16 through FIG. 18, it becomes possible to form a variety of cone frustum shapes with ease by appropriately varying a size of the cutout or a diameter of the heat-dissipating plate A6 or the print substrate A2.

The process may be that the heat-dissipating plate A6 is previously attached to the print substrate A2 in which the LEDs A1 are implanted in a condition, for example, in a tabular state prior to curving, next one side A2a of the cutout and the other side A2b of the cutout are jointed or proximately held to locate the illuminant loading face A2c in a concave side, and then the print substrate A2 and the heat-dissipating plate A6 are held by the holding groove A33 that is provided on the lighting case A4 and that has a diameter corresponding to the print substrate A2 and the heat-dissipating plate A6.

Next a fifth embodiment of the present claimed invention will be explained with referring to FIG. 19 and FIG. 20. Same codes will be given to components in this embodiment corresponding to the components in the forth embodiment.

The lighting unit A4 in accordance with the embodiment, like the above embodiment, comprises LEDs A1 as a plurality of illuminants, a print substrate A2 that is in a toric shape having a cutout at a part thereof and that can be curved along a direction of its thickness and a lighting case A3 as a holding frame that has a center hole A32 for visual inspection or filming and that holds the print substrate A2.

Like the above embodiment, first the print substrate A2 is held in a tabular state and a plurality of LEDs A1 are implanted all over an illuminant loading face A2c set on one of the faces of the print substrate A2 with soldering or the like. Then one side A2a of the cutout and the other side A2b of the cutout of the print substrate A2 are jointed or proximately held so as to locate the illuminant loading face A2c in a concave side and the print substrate A2 is held by a holding groove A33 that is arranged on the lighting case A3 and that has a diameter corresponding to the print substrate A2. Consequently the print substrate A2 is formed to be in a shape of a cone frustum and the illuminant loading face A2c is a concave face of the cone frustum on which the LEDs A1 are arranged. A power cable A5 is also wired on the print substrate A2 with soldering.

Figure 19:
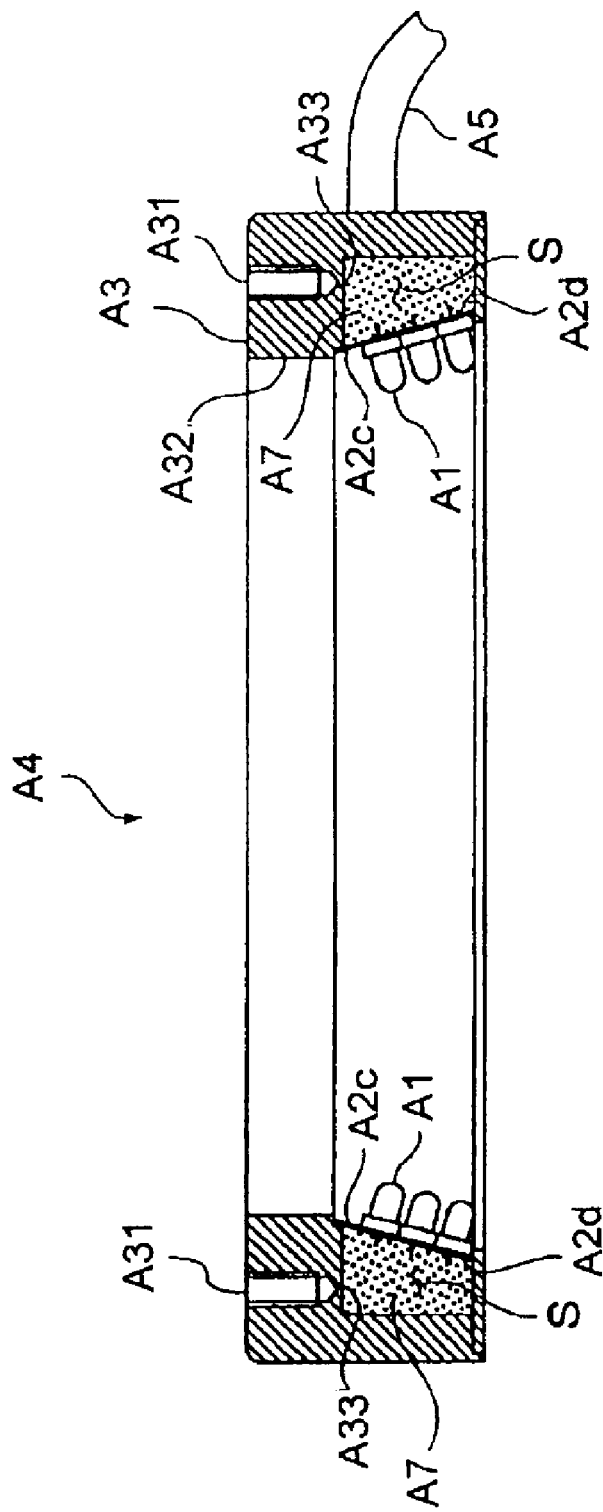
FIG. 19 is a central longitudinal cross-sectional view of a lighting system in accordance with another embodiment of the present claimed invention.
Figure 20:
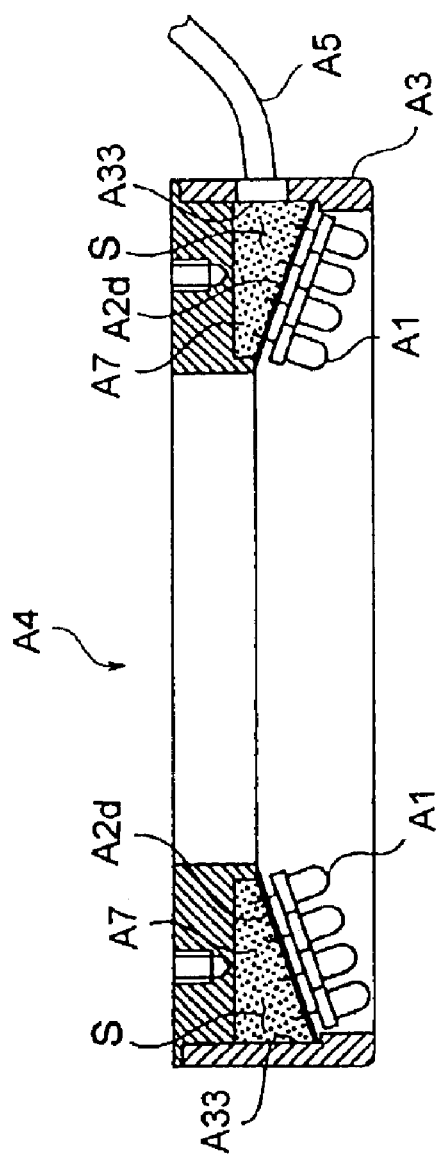
FIG. 20 is a central longitudinal cross-sectional view of a lighting system in accordance with a modified form of the embodiment.

In this embodiment, as shown in FIG. 19 and FIG. 20, a heat-dissipating member A7 that is liquid or gelled at least at a time to fill the heat-dissipating member A7 is filled or generally filled in a sealed space S formed between a back face A2d of the illuminant loading face A2c of the print substrate A2 and the holding groove A33 from a fill opening, not shown in drawings, and the heat-dissipating member A7 tightly attaches to the back face A2d of the illuminant loading face A2c and the holding groove A33.

It is a matter of course that the heat-dissipating member A7 may be previously filled or generally filled in the holding groove A3 and then the print substrate A2 may be mounted on the lighting case A3.

The lighting unit and the method for manufacturing the lighting unit in accordance with the present claimed invention is not limited to the above-described forth and fifth embodiments and may be variously varied.

For example, the illuminant loading face is not limited to a concave face of a cone frustum, but may be an inner face of a cylinder. In this case, it is a matter of course that a heat-dissipating plate and a print substrate have to be strip-shaped in a tabular state so as to correspond to the shape of the illuminant loading face.

In addition the print substrate may be first curved to be in a shape of a cone frustum and then LEDs may be mounted on a concave face of the cone frustum.

Further, a plurality of slits extending toward a radial direction may be intermittently arranged on a periphery of the print substrate. In accordance with the arrangement, it is possible to curve the print substrate with ease.

A wire of the print substrate thicker than a wire usually required for an electric current may be used so that an effect of heat dissipation can be performed by the wire itself. In accordance with the arrangement, the effect of heat dissipation can be further increased. More concretely, from an effective heat dissipation standpoint, it is preferable that a width of the wiring connected with a lead wire extending from the holding body that holds light emitting element (bare chip) of the LEDs is made wider.

The illuminant loading face may be formed by processing the holding frame itself as conventionally, LEDs may be arranged on the illuminant loading face and then a heat-dissipating plate or a heat-dissipating member like the above embodiment may be arranged.

Each concrete arrangement is not limited to the above-mentioned embodiment, and there may be various modifications without departing from a spirit of the present claimed invention.

As mentioned above, in accordance with the present claimed invention, since the back face of the illuminant loading member and the holding frame can be joined in a surface-wise manner through the heat-dissipating member, it is possible to transmit heat generated from the illuminants effectively and quickly to the holding frame, thereby to dissipate the heat by making use of whole the holding frame. As a result of this, it is possible to pass a strong electric current through the illuminants so as to obtain a strong luminous intensity and the luminous intensity can be stabilized and the life duration can be elongated.

Further, since it is possible for the heat-dissipating member to tightly attach to both the curved illuminant loading face and the supporting face of the holding frame with ease because of its flexibility and elasticity, manufacturing and assembling process can be simplified.

In addition, since the heat-dissipating member tightly attaches to the illuminant loading face and the holding frame, a chance of the illuminant loading member getting loose will be reduced, which keeps a condition of the loaded illuminant in an improved state, thereby to contribute improvement of the quality of light irradiation or a quality of the lighting.

Since it is possible to form the concave face of the cone frustum that can tightly attach to the back face of the illuminant loading face just by jointing or proximately holding one side of the cutout of the heat-dissipating member and other side of the cutout, heat can be dissipated with ease from the illuminants arranged on the curved concave face. As a result of this, the temperature of the illuminants can be lowered effectively by dissipating the heat from the illuminants, thereby to suppress temperature rise of the illuminants. As a result of this, high luminous intensity can be obtained and life duration of the lighting unit can be extended.

It is a matter of course that there is no need of arranging a hole for implanting the illuminants on a holding frame and the illuminants and wiring can be provided on the concave face of the cone frustum shape with ease, thereby to simplify a manufacturing method.

Further, it becomes possible to form a variety of cone frustum shapes with ease by varying a size of the cutout or a diameter of the heat-dissipating member or the print substrate.

What is claimed is:

1. A light irradiating unit comprises
   an illuminant loading member that has illuminant loading face that can be curved and on which a plurality of illuminants are loaded,
   a holding frame having a curved supporting face that holds the illuminant loading member and
   a tabular heat-dissipating member having at least a surface flexible and adhesive to enable the surface to tightly attach to a back face of the illuminant loading face by transforming itself to conform and wrap around a lead wire of the illuminant or an electronic component projecting from the back side of the illuminant loading face, the tabular heat-dissipating member has a characteristic of keeping its shape along a direction of its thickness when affixed on the curved illuminant loading face,
   and characterized by the heat-dissipating member being generally tightly attached to the back face of the illuminant loading face and the supporting face of the holding frame that faces to the back face of the illuminant loading face respectively and the illuminant loading face is held in a curved state along the supporting face.

2. The light irradiating unit described in claim 1, wherein a surface of the heat-dissipating member is no fewer than 10 degrees and no more than 30 degrees in an Asker C hardness that indicates flexibility.

3. The light irradiating unit described in claim 1, wherein the supporting face of the holding a frame is a concave face of a cone frustum shape, the illuminant loading member is a print substrate that can be curved along a direction of thickness and that has a toric shape having a cutout at a part thereof in a tabular state or a generally tabular state and, one face of the print substrate is set as the illuminant loading face, the illuminant loading face is formed to be a concave face of a cone frustum shape by jointing or proximately holding one side of the cutout of the illuminant loading member and the other side of the cutout so that the illuminant loading face locates in the concave face.

4. A lighting unit comprising
   a plurality of illuminants,
   a toric print substrate that can be curved along a direction of its thickness and that has a cutout at a part thereof in a tabular state or a generally tabular state and plurality of the illuminants are mounted on an illuminant loading face set on one face of the print substrate,
   a heat-dissipating member that is in a same shape or in a generally same shape in a plane view as that of the print substrate and at least a surface of the heat-dissipating member is so flexible and adhesive that the surface can tightly attach to a back face of the illuminant loading face by transforming itself to dent so as to wrap around a lead wire of the illuminant or an electronic component projecting from the back side of the illuminant loading face, the heat-dissipating member has a characteristic of keeping its shape, curving alone a direction of its thickness when placed on a tabular surface, and
   a holding frame that has a supporting face in a shape of a concave face of a cone frustum, and
   characterized by the print substrate is being held in a tabular state or a generally tabular state and a plurality of illuminants are loaded on the illuminant loading face, and then one side of the cutout of the print substrate loaded with the illuminants and the other side of the cutout are jointed or proximately held to form the print substrate in a shape of a cone frustum so that the illuminant loading face locates in a concave side, or that one side of the cutout of the print substrate and the other side of the cutout are jointed or proximately held to form the print substrate in a shape of a cone frustum so that the illuminant loading face locates in a concave side, and then a plurality of illuminants are loaded on the illuminant loading face,
   and the heat-dissipating member is formed to be in a shape of a cone frustum by jointing or proximately holding one side of a cutout provided on the heat-dissipating member and the other side of the cutout, and the heat-dissipating member is generally tightly attached to a back face of the illuminant loading face and the supporting face of the holding frame that faces to the back face of the illuminant loading face is held in a curved state along the supporting face.

5. A lighting unit comprising
   a plurality of illuminants,
   a toric print substrate curved along a direction of its thickness and that has a cutout at a part thereof in a tabular state or a generally tabular state and the plurality of the illuminants are mounted on an illuminant loading face on one face of the print substrate,
   a heat-dissipating member that is in a same shape or in a generally same shape in a plane view as that of the print substrate and at least a surface of the heat-dissipating member is sufficiently flexible and adhesive to tightly attach to a back face of the illuminant loading face by transforming itself to bend around a lead wire of the illuminant or an electronic component projecting from the back side of the illuminant loading face, the heat-dissipating member has a characteristic of keeping its shape as it is curved along a direction of its thickness when placed on a tabular surface, and a holding frame that has a supporting face in a shape of a concave face of a cone frustum, characterized by the print substrate being held in a tabular state or a generally tabular state and a plurality of illuminants are loaded on an illuminant loading face set on one of the faces thereof, the faces of the heat-dissipating member is attached to the back face of the illuminant loading face, one side of the cutout of the print substrate and the other side of the cutout are jointed or proximately held to form the print substrate in a shape of a cone frustum so that the illuminant loading face locates in a concave side, and the heat-dissipating member is tightly attached to the supporting face so that the illuminant loading face is held in a curved state along the supporting face.

6. A light irradiating unit comprising:

a plurality of light emitting diodes (LEDS);

a holding member having a surface in the shape of a hollow truncated cone that operatively mounts the LEDS to enable an application of electrical power;

a toric shaped heat-dissipating flexible member adhered on one side to the holding member, the heat-dissipating flexible member is electrically non-conducting and has a surface characteristic of conforming to indentations and projections of the holding member to maximize surface contact to facilitate heat dissipation from LEDS and;

a case with an annular cone frustum supporting face adhered to another side of the toric shaped heat-dissipating flexible member.

7. The light irradiating unit of claim 6 when the heat-dissipating flexible member includes silicone rubber.

8. The light irradiating unit of claim 7 wherein the silicone rubber contains no more than 300 ppm siloxane.

9. The light irradiating unit of claim 7 where the holding member is a flexible member with an electrical pattern of conductors provided thereon, the holding member mounts the LEDS on one surface to contact the conductors and the other surface is non-planar and is adhered to the heat-dissipating flexible member.

10. A method for manufacturing a lighting unit having a plurality of illuminants, a toric print substrate that can be curved along a direction of its thickness and that has a cutout at a part thereof in a tabular state or a generally tabular state and the plurality of the illuminants can be mounted on an illuminant loading face set on one face of the toric print substrate, a heat-dissipating member that is in a same shape or in a generally same shape in a plane view as that of the toric print substrate and at least a surface of the heat-dissipating member is flexible and adhesive so that the surface can tightly attach to a back face of the illuminant loading face by transforming itself to dent so as to wrap around a lead wire of the illuminant or an electronic component projecting from the back side of the illuminant loading face, the heat-dissipating member can be curved along a thickness direction when placed on a tabular surface, and a holding frame that has a supporting face in a shape of a concave face of a cone frustum, comprising:

holding the print substrate in a tabular state or in a generally tabular state, loading a plurality of illuminants on the illuminant loading face, and then one side of the cutout of the print substrate loaded with the illuminants and the other side of the cutout are joined or proximately held together to form the toric print substrate in a shape of a cone frustum so that the illuminant loading face locates in a concave side, or that one side of the cutout of the print substrate and the other side of the cutout are joined or proximately held together to form the toric print substrate in a shape of a cone frustum so that the illuminant loading face locates in a concave side, and then a plurality of illuminants are loaded on the illuminant loading face, and the heat-dissipating member is formed in a shape of a cone frustum by jointing or proximately holding one side of a cutout provided on the heat-dissipating member and the other side of the cutout, and the heat-dissipating member is generally tightly attached to the back face of the illuminant loading face and the supporting face of the holding frame that faces to the back face of the illuminant loading face respectively and the illuminant loading face is held in a curved state along the supporting face.

11. A method for manufacturing a lighting unit comprising a plurality of illuminants, a toric print substrate that can be curved along a direction of its thickness and that has a cutout at a part thereof in a tabular state or a generally tabular state and the plurality of the illuminants can be mounted on an illuminant loading face set on one face of the print substrate, a heat-dissipating member that is in a same shape or in a generally same shape in a plane view as that of the toric print substrate and at least a surface of the heat-dissipating member is flexible and adhesive to enable the surface to tightly attach to a back face of the illuminant loading face by transforming itself to dent so as to wrap around a lead wire of the illuminant or an electronic component projecting from the back side of the illuminant loading face, the, shape of the heat-dissipating member is maintained while curved along a direction of the thickness of the heat-dissipating member when placed on a tabular surface and that can be curved along a direction of the tabular thickness, and a holding frame that has a supporting face in a shape of a concave face of a cone frustum, and characterized by the toric print substrate being curved along a direction of the toric print substrate thickness and that has a cutout at a part thereof held in a tabular state or a generally tabular state, a plurality of the illuminants are loaded on an the illuminant loading face set on one of the faces thereof, the heat-dissipating member that is in a same shape or in a generally same shape in a plane view as that of the print substrate is curved and tightly attached to a the back face of the illuminant loading face of the toric print substrate, and one side of the cutout of the print substrate loaded with the illuminants and the other side of the cutout are joined or proximately held to form a shape of a cone frustum so that the illuminant loading face locates in a concave side, and the heat-dissipating member is generally tightly attached to the supporting face of the holding frame and the illuminant loading face is held in a curved state along the supporting face.

12. A method of manufacturing a lighting unit for inspecting a surface, the lighting unit having an opening at the center thereof for visually inspecting the surface to be inspected, wherein said method comprises the steps of:

providing a flexible circular printed substrate having a concentric circular hole and a cutout which has at least two sides in a planar state, embedding a plurality of illuminants in said printed circuit board, joining one side of the cutout and the other side of the cutout of said printed substrate or holding both sides in close contact so as to form the printed substrate into a shape of a hollow truncated cone with the plurality of illuminants placed in a side of a concave face of said printed substrate;

providing a solid tone shape heat-dissipating member with an opening, the solid toric shape heat-dissipating member having adhering surfaces;

providing a case with a center hole and a annular cone frustum supporting face;

tightly attaching the printed substrate to the annular cone frustum supporting face with the solid tone shape heat-dissipating plate; and positioning a frame about said printed substrate and retaining said printed substrate in said shape of a hollow truncated cone as to obtain the lighting unit in which the plurality of illuminants are arranged on the concave face of the printed substrate formed into the shape of a hollow truncated cone.

\* \* \* \* \*